United States Patent
Klingler et al.

(10) Patent No.: US 6,743,790 B2
(45) Date of Patent: Jun. 1, 2004

(54) FACTOR VIIA INHIBITORY (THIO)UREA DERIVATIVES, THEIR PREPARATION AND THEIR USE

(75) Inventors: Otmar Klingler, Rodgau (DE); Manfred Schudok, Eppstein/Ts. (DE); Hans-Peter Nestler, Kelkheim (DE); Hans Matter, Langenselbold (DE); Herman Schreuder, Hofheim-Lorsbach (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/874,318

(22) Filed: Jun. 6, 2001

(65) Prior Publication Data

US 2002/0052417 A1 May 2, 2002

(30) Foreign Application Priority Data

Jun. 6, 2000 (EP) .............................. 00112116

(51) Int. Cl.$^7$ ...................... A61K 31/535; A61K 31/17; A61K 31/445; C07D 213/58; C07C 275/00
(52) U.S. Cl. ................. 514/230.8; 514/237.8; 514/327; 514/330; 514/331; 514/354; 514/357; 514/364; 514/371; 514/452; 514/586; 514/597; 544/159; 544/160; 544/162; 544/165; 546/224; 546/233; 546/237; 546/332; 548/185; 564/27; 564/28; 564/29; 564/51; 549/366
(58) Field of Search .......................... 564/38, 27, 28, 564/29, 51; 546/235, 227, 233, 237, 224, 332; 514/330, 586, 597, 452, 369, 371, 327, 331, 354, 357, 230.8, 237.8; 544/159, 165, 160, 162, 105; 549/366; 548/185

(56) References Cited

U.S. PATENT DOCUMENTS

| | | | |
|---|---|---|---|
| 5,273,982 A | * 12/1993 | Alig et al. ................... | 514/315 |
| 5,314,902 A | 5/1994 | Tjoeng et al. ............... | 514/357 |
| 5,703,050 A | 12/1997 | Klingler et al. .............. | 514/18 |

FOREIGN PATENT DOCUMENTS

| | | | |
|---|---|---|---|
| EP | 0 987 274 A1 | 3/2000 | ............ C07K/5/11 |
| WO | WO 92/06711 A1 | 4/1992 | ......... A61K/39/395 |
| WO | WO 94/17041 A1 | 8/1994 | ......... C07D/213/55 |
| WO | WO 94/22907 A1 | 10/1994 | ............ C07K/5/06 |
| WO | WO 96/12800 A1 | 5/1996 | ............ C12N/9/48 |
| WO | WO 97/47651 A1 | 12/1997 | ......... C07K/14/745 |

OTHER PUBLICATIONS

G.J. Broze, Jr., "Tissue factor pathway inhibitor and the current concept of blood coagulation" *Blood Coagulation and Fibrionolysis* 6(1):S7–S13 (1995).

Y.-C. Cheng and W.H. Prusoff, "Relationship between the inhibition constant ($K_i$) and the concentration of inhibitor which causes 50 per cent inhibition ($I_{50}$) of an enzymatic reaction" *Biochemical Pharmacology* 22:3099–3108 (1973).

H. Cole, "The tissue factor pathway of coagulation" *Australian Journal of Medical Science* 16:87–93 (1995).

L.A. Harker, et al., "Antithrombotic Benefits and Hemorrhagic Risks of Direct Thrombin Antagonists" *Thrombosis and Haemostasis* 74(1):464–472 (1995).

L.A. Harker, et al., "Antithrombotic and Antilesion Benefits without Hemorrhagic Risks by Inhibiting Tissue Factor Pathway" *Haemostasis* 26(Suppl. 1):76–82 (1996).

J.A. Ostrem et al., "Discovery of a Novel, Potent, and Specific Family of Factor Xa Inhibitors via Combinatorial Chemistry" *Biochemistry* 37:1053–1059 (1998).

I,H. Segel, Chapter 3, "Simple Inhibition Systems," in *Enzyme Kinetics: Behavior and Analysis of Rapid Equilibrium and Steady–State Enzyme Systems*, John Wiley & Sons, New York, p. 100–125 (1975).

Jang, Y. et al. "Influence of Blockade at Specific Levels of the Coagulation Cascade on Restenosis in a Rabbit Atherosclerotic Femoral Artery Injury Model" *Circulation* 92:3041–50 (1995).

* cited by examiner

*Primary Examiner*—D. Margaret Seaman
*Assistant Examiner*—Raymond Covington
(74) *Attorney, Agent, or Firm*—Finnegan, Henderson, Farabow, Garrett & Dunner, L.L.P.

(57) ABSTRACT

The present invention relates to compounds of the formula I,

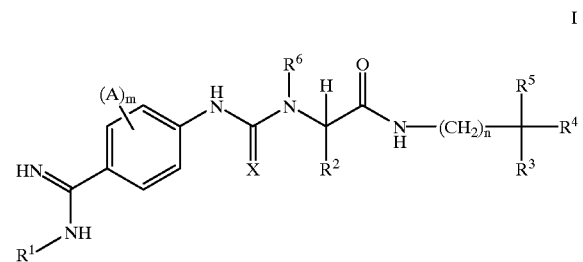

in which $R^1$, $R^2$, $R^3$, $R^4$, $R^5$, $R^6$, A, X, m and n have the meanings indicated in the claims. The compounds of the formula I are valuable pharmacologically active compounds. They exhibit a strong antithrombotic effect and are suitable, for example, for the therapy and prophylaxis of thromboembolic diseases and restenoses. They are reversible inhibitors of the blood clotting enzyme factor VIIa and can in general be applied in conditions in which an undesired activity of factor VIIa is present or for the cure or prevention of which an inhibition of factor VIIa is intended. The invention furthermore relates to processes for the preparation of compounds of the formula I, their use, for example as active ingredients in pharmaceuticals, and pharmaceutical preparations comprising them.

12 Claims, No Drawings

FACTOR VIIA INHIBITORY (THIO)UREA DERIVATIVES, THEIR PREPARATION AND THEIR USE

This application claims the benefit of priority under 35 U.S.C. §119(a) to European Patent Application No. 00112116.9, filed Jun. 6, 2000, the disclosure of which is hereby incorporated by reference.

TECHNICAL FIELD

The present invention relates to compounds of the formula I,

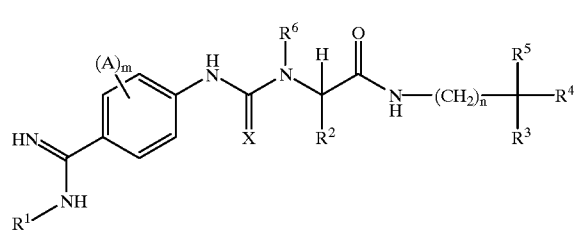

in which $R^1$, $R^2$, $R^3$, $R^4$, $R^5$, $R^6$, A, X, m and n have the meanings indicated below. The compounds of the formula I are valuable pharmacologically active compounds. They exhibit a strong antithrombotic effect and are suitable, for example, for the therapy and prophylaxis of thromboembolic diseases and restenoses. They are reversible inhibitors of the blood clotting enzyme factor VIIa and can in general be applied in conditions in which an undesired activity of factor VIIa is present or for the cure or prevention of which an inhibition of factor VIIa is intended. The invention furthermore relates to processes for the preparation of compounds of the formula I, their use, for example as active ingredients in pharmaceuticals, and pharmaceutical preparations comprising them.

BACKGROUND OF THE INVENTION

The ability to form blood clots is vital to survival. The formation of a blood clot or a thrombus is normally the result of tissue injury which initiates the coagulation cascade and has the effect of slowing or preventing blood flow in wound healing. Other factors which are not directly related to tissue injury like atherosclerosis and inflammation may also initiate the coagulation cascade. In general, a relationship exists between inflammation and the coagulation cascade. Inflammation mediators regulate the coagulation cascade and coagulation components influence the production and activity of inflammation mediators. However, in certain disease states the formation of blood clots within the circulatory system reaches an undesired extent and is itself the source of morbidity potentially leading to pathological consequences. It is nevertheless not desirable in such disease states to completely inhibit the blood clotting system because life threatening hemorrhage would ensue. In the treatment of such states a well-balanced intervention into the blood clotting system is required, and there is still a need for substances exhibiting a suitable pharmacological activity for achieving such a result.

Blood coagulation is a complex process involving a progressively amplified series of enzyme activation reactions in which plasma zymogens are sequentially activated by limited proteolysis. Mechanistically the blood coagulation cascade has been divided into intrinsic and extrinsic pathways, which converge at the activation of factor X; subsequent generation of thrombin proceeds through a single common pathway (see Scheme 1). Present evidence suggests that the intrinsic pathway plays an important role in the maintenance and growth of fibrin formation, while the extrinsic pathway is critical in the initiation phase of blood coagulation (H. Cole, Aust. J. Med. Sci. 16 (1995) 87; G. J. Broze, Blood Coagulation and Fibrinolysis 6, Suppl. 1 (1995) S7; which is incorporated herein by reference). It is generally accepted that blood coagulation is physically initiated upon formation of a factor VIIa/tissue factor (TF) complex. Once formed, this complex rapidly initiates coagulation by activating factors IX and X. The newly generated activated factor X, i.e. factor Xa, then forms a one-to-one complex with factor Va and phospholipids to form a prothrombinase complex, which is responsible for converting soluble fibrinogen to insoluble fibrin via the activation of thrombin from its precursor prothrombin. As time progresses, the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor. In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin. The autocatalytic nature of thrombin generation is an important safeguard against uncontrolled bleeding and it ensures that, once a given threshold level of prothrombinase is present, blood coagulation will proceed to completion. Thus, it is most desirable to develop agents that inhibit coagulation without directly inhibiting thrombin but by inhibiting other steps in the coagulation cascade like factor VIIa activity.

Scheme 1
Blood coagulation cascade

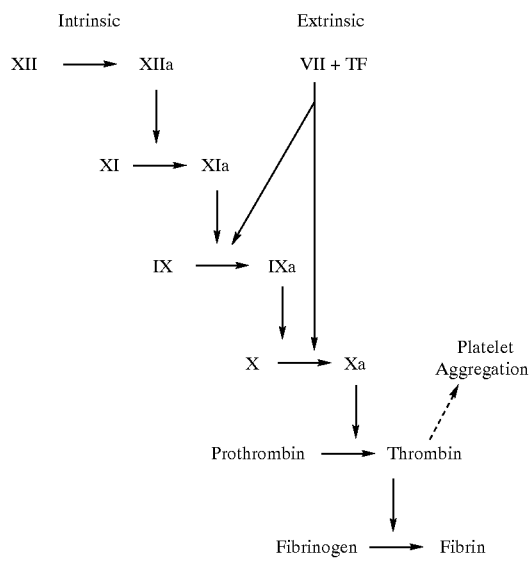

In many clinical applications there is a great need for the prevention of intravascular blood clots or for some anticoagulant treatment. For example, nearly 50% of patients who have undergone a total hip replacement develop deep vein thrombosis (DVT). The currently available drugs like heparin and derivatives thereof are not satisfactory in many specific clinical applications. The currently approved therapies include fixed dose low molecular weight heparin (LMWH) and variable dose heparin. Even with these drug regimes 10% to 20% of patients develop DVT, and 5% to 10% develop bleeding complications.

Another clinical situation for which better anticoagulants are needed concerns subjects undergoing transluminal coronary angioplasty and subjects at risk for myocardial infarction or suffering from crescendo angina. The present, conventionally accepted therapy which consists of administering heparin and aspirin, is associated with a 6% to 8% abrupt vessel closure rate within 24 hours of the procedure. The rate of bleeding complications requiring transfusion therapy due to the use of heparin also is approximately 7%. Moreover, even though delayed closures are significant, administration of heparin after termination of the procedures is of little value and can be detrimental.

The widely used blood-clotting inhibitors like heparin and related sulfated polysaccharides like LMWH and heparin sulfate exert their anti-clotting effects by promoting the binding of a natural regulator of the clotting process, antithrombin III, to thrombin and to factor Xa. The inhibitory activity of heparin primarily is directed toward thrombin which is inactivated approximately 100 times faster than factor Xa. Hirudin and hirulog are two additional thrombin-specific anticoagulants presently in clinical trials. However, these anticoagulants which inhibit thrombin also are associated with bleeding complications. Preclinical studies in baboons and dogs have shown that targeting enzymes involved at earlier stages of the coagulation cascade, such as factor Xa or factor VIIa, prevents clot formation without producing the bleeding side effects observed with direct thrombin inhibitors (L. A. Harker et al., Thromb. Haemostas. 74 (1995) 464; incorporated herein by reference).

Specific inhibition of the factor VIIa/tissue factor catalytic complex using monoclonal antibodies (for example, WO-A-92/06711; incorporated herein by reference) or a protein such as chloromethyl ketone inactivated factor VIIa (for example, WO-A-96/12800 and WO-A-97/47651; both of which are incorporated herein by reference) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty (L. A. Harker et al., Haemostasis 26 (1996) S1:76; incorporated herein by reference). Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition (L. A. Harker et al., Thromb. Haemostas. 74 (1995) 464; incorporated herein by reference).

A specific inhibitor of factor VIIa which has a favorable property profile would have substantial practical value in the practice of medicine. In particular, a factor VIIa inhibitor would be effective under circumstances where the present drugs of choice, like heparin and related sulfated polysaccharides, are ineffective or only marginally effective. Certain inhibitors of factor VIIa have already been described. EP-A-987274 (incorporated herein by reference), for example, discloses compounds containing a tripeptide unit which inhibit factor VIIa. However, the property profile of these compounds is still not ideal, and there is a need for further low molecular weight factor VIIa-specific blood clotting inhibitors that are effective and do not cause unwanted side effects. The present invention satisfies this need by providing novel factor VIIa activity inhibiting urea derivatives and thiourea derivatives of the formula I. Other (thio)urea derivatives have already been described, for example, in U.S. Pat. No. 5,314,902 (corresponding to WO-A-94/17041) and U.S. Pat. No. 5,703,050 (corresponding to WO-A-94/22907), the disclosures of which are herein incorporated by reference, however, the disclosed compounds are antagonists of integrin receptors like the fibrinogen receptor GPIIb/IIIa.

SUMMARY AND DETAILED DESCRIPTION

Thus, a subject of the present invention is a compound of the formula I

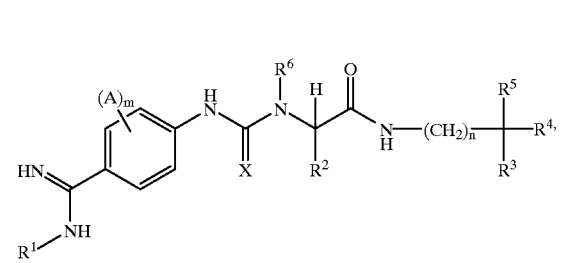

wherein m is 0, 1, 2, 3, or 4;

n is 0, 1, 2, or 3;

A is halogen;

X is sulfur or oxygen;

$R^1$ is chosen from hydrogen, hydroxy, $(C_1-C_{12})$-alkoxycarbonyl-, $(C_6-C_{14})$-aryl-$(C_1-C_4)$-alkoxycarbonyl-, and $(C_6-C_{14})$-aryloxycarbonyl-, wherein each of the aryl groups is unsubstituted or substituted by at least one identical or different substituent chosen from $(C_1-C_{12})$-alkyl, halogen, and $(C_1-C_{12})$-alkoxy;

$R^2$ is chosen from hydrogen, $(C_1-C_{12})$-alkyl, $(C_6-C_{14})$-aryl, $(C_6-C_{14})$-aryl-$(C_1-C_4)$-alkyl-, $R^{20}$—$(C_1-C_{12})$-alkyl-, $R^{20}$—$(C_6-C_{14})$-aryl-, and $R^{20}$—$(C_6-C_{14})$-aryl-$(C_1-C_4)$-alkyl-, wherein $R^{20}$ is chosen from hydroxycarbonyl-, aminocarbonyl-, $(C_1-C_{12})$-alkoxycarbonyl-, and $(C_6-C_{14})$-aryl-$(C_1-C_4)$-alkoxycarbonyl-;

$R^3$ is chosen from hydrogen, cyano, hydroxy, and $(C_1-C_{12})$-alkyl;

$R^4$ is chosen from $(C_1-C_{12})$-alkyl, $(C_6-C_{14})$-aryl, $(C_6-C_{14})$-aryl-$(C_1-C_4)$-alkyl-, Het, and Het-$(C_1-C_4)$-alkyl-, wherein the alkyl, aryl and Het groups are unsubstituted or substituted by at least one identical or different substituent $R^{10}$;

$R^5$ is chosen from hydrogen, $(C_1-C_{12})$-alkyl, $(C_6-C_{14})$-aryl, $(C_6-C_{14})$-aryl-$(C_1-C_4)$-alkyl-, Het, Het-$(C_1-C_4)$-alkyl-, $(C_6-C_{14})$-aryl-$(C_1-C_4)$-alkyl-aminocarbonyl-, and Het-$(C_1-C_4)$-alkyl-aminocarbonyl-, wherein the alkyl, aryl and Het groups are unsubstituted or substituted by at least one identical or different substituent $R^{10}$;

or $R^4$ and $R^5$ together with the carbon atom to which they are bonded form a saturated or unsaturated 3-membered to 8-membered ring which is a carbocyclic ring or a heterocyclic ring containing 1, 2 or 3 identical or different ring heteroatoms chosen from nitrogen, oxygen and sulfur, and which is optionally condensed to one or two saturated or unsaturated carbocyclic ring systems or heterocyclic ring systems containing 5 to 10 ring atoms of which 1, 2 or 3 are identical or different ring heteroatoms chosen from nitrogen, oxygen and sulfur, wherein the resulting $R^4(R^5)C$ group is unsubstituted or substituted by at least one identical or different substituent $R^{10}$;

$R^6$ is chosen from hydrogen, hydroxy, $(C_1-C_8)$-alkoxy, and $(C_6-C_{14})$-aryl-$(C_1-C_4)$-alkoxy-;

$R^{10}$ is chosen from $(C_1-C_{12})$-alkyl, $(C_6-C_{14})$-aryl-$(C_1-C_4)$-alkyl-, $(C_1-C_8)$-alkoxy, $(C_1-C_4)$-alkoxy-$(C_2-C_4)$-alkoxy-, $(C_6-C_{14})$-aryl-$(C_1-C_4)$-alkoxy-, $(C_6-C_{14})$-aryloxy-, Het-oxy-, Het-$(C_1-C_4)$-alkoxy-, $(C_6-C_{14})$-aryl, Het, Het-$(C_1-C_4)$-alkyl-, trifluoromethoxy, trifluoromethyl, halogen, oxo, hydroxy, amino, $(C_1-C_{12})$-alkylcarbonylamino-, aminocarbonylamino-, $(C_6-C_{14})$-arylcarbonylamino-, Het-carbonylamino-, $(C_6-C_{14})$-aryl-$(C_1-C_4)$-alkylcarbonylamino-, Het-$(C_1-C_4)$-alkylcarbonylamino-, $(C_1-C_8)$-alkylcarbonyl-, $(C_6-C_{14})$-arylcarbonyl-, $(C_1-C_8)$-alkylaminocarbonyl-, $(C_6-C_{14})$-arylaminocarbonyl-, $(C_6-C_{14})$-aryl-$(C_1-C_4)$-alkylaminocarbonyl-, Het-aminocarbonyl-, Het-$(C_1-C_4)$-alkylaminocarbonyl-, aminocarbonyl-, $(C_1-C_8)$-alkoxycarbonyl-, hydroxycarbonyl-, cyano, nitro, amidino, acetimino, tri-$((C_1-C_4)$-alkyl)ammonio-, $(C_1-C_8)$-alkylamino-, di-$((C_1-C_8)$-alkyl)amino-, hydroxycarbonylmethoxy-, $(C_1-C_8)$-alkylsulfonyl-, $(C_6-C_{14})$-arylsulfonyl-, $(C_1-C_5)$-alkylaminosulfonyl-, $(C_6-C_{14})$-arylaminosulfonyl-, $(C_6-C_{14})$-aryl-$(C_1-C_4)$-alkylaminosulfonyl-, Het-aminosulfonyl-, Het-$(C_1-C_4)$-alkylaminosulfonyl-, $(C_1-C_8)$-alkylsulfonylamino-, $(C_6-C_{14})$-arylsulfonylamino-, $(C_6-C_{14})$-aryl-$(C_1-C_4)$-alkylsulfonylamino-, Het-sulfonylamino-, and Het-$(C_1-C_4)$-alkylsulfonylamino-, wherein $(C_1-C_{12})$-alkylcarbonylamino- representing $R^{10}$ is unsubstituted or substituted in the alkyl group by a substituent chosen from amino, hydroxy and $(C_1-C_4)$-alkoxy, and wherein $(C_1-C_{12})$-alkyl and $(C_1-C_8)$-alkoxy representing $R^{10}$ are unsubstituted or substituted by at least one identical or different substituent chosen from $(C_1-C_8)$-alkoxycarbonyl-, hydroxycarbonyl-, and aminocarbonyl-, wherein each of the aryl groups and Het group in a group $R^{10}$ is unsubstituted or substituted by at least one identical or different substituent chosen from halogen, nitro, oxo, hydroxy, $(C_1-C_8)$-alkyl, $(C_1-C_8)$-alkoxy, $(C_1-C_4)$-alkoxy-$(C_2-C_4)$-alkoxy-, $(C_6-C_{14})$-aryloxy-, $(C_6-C_{14})$-aryl-$(C_1-C_4)$-alkoxy-, Het-oxy-, Het-$(C_1-C_4)$-alkoxy-, $(C_6-C_{14})$-aryl, $(C_6-C_{14})$-aryl-$(C_1-C_4)$-alkyl-, Het, Het-$(C_1-C_4)$-alkyl-, trifluoromethyl, cyano, trifluoromethoxy, $(C_1-C_8)$-alkylsulfonyl-, $(C_1-C_8)$-alkoxycarbonyl-, hydroxycarbonyl-, aminocarbonyl-, amino, $(C_1-C_8)$-alkylamino-, di-$((C_1-C_8)$-alkyl)amino-, $(C_1-C_8)$-alkylcarbonylamino-, $(C_6-C_{14})$-aryl-$(C_1-C_4)$-alkylcarbonylamino-, $(C_6-C_{14})$-arylcarbonylamino-, Het-carbonylamino-, Het-$(C_1-C_4)$-alkylcarbonylamino-, and $(C_1-C_8)$-alkylcarbonyl-, wherein $(C_1-C_8)$-alkyl and $(C_1-C_8)$-alkoxy representing a substituent on an aryl group or Het group in a group $R^{10}$ are unsubstituted or substituted by at least one identical or different substituent chosen from $(C_1-C_8)$-alkoxycarbonyl-, hydroxycarbonyl-, and aminocarbonyl-, with the proviso that, when a substituent $R^{10}$ is bonded to an alkyl group, it cannot be $(C_1-C_8)$-alkoxycarbonyl-, hydroxycarbonyl-, aminocarbonyl-, $(C_1-C_8)$-alkylaminocarbonyl- or $(C_1-C_8)$-alkylaminosulfonyl-, and that, when a substituent $R^{10}$ is bonded to an alkyl group, it cannot be $(C_1-C_8)$-alkyl which is substituted by at least one identical or different substituents chosen from $(C_1-C_8)$-alkoxycarbonyl-, hydroxycarbonyl- and aminocarbonyl-;

Het is a residue of a saturated or unsaturated monocyclic or bicyclic, 3-membered to 10-membered heterocyclic ring system containing 1, 2 or 3 identical or different ring heteroatoms chosen from nitrogen, oxygen and sulfur;

or a physiologically tolerable salt thereof, in any stereoisomeric form, or a mixture of any such compounds in any ratio.

All groups, substituents, residues etc. which can occur several times in the compounds of the formula I, for example A, $R^{10}$ or Het, can each independently of one another have the meanings indicated, and can in each case be identical or different.

As used herein, the term alkyl is to be understood in the broadest sense to mean hydrocarbon residues which can be linear, i.e. straight-chain, or branched and which can be acyclic or cyclic groups or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another group or is substituted, for example in an alkoxy group (alkyl-O—), an alkoxycarbonyl- group or an arylalkyl- group. Non limiting examples of alkyl groups containing 1, 2, 3, 4, 5, 6, 7, 8, 9, 10, 11, or 12 carbon atoms are methyl, ethyl, propyl, butyl, pentyl, hexyl, heptyl, octyl, nonyl, decyl, undecyl, dodecyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl, tert-pentyl, 2,3,4-trimethylhexyl, and isodecyl.

Unsaturated alkyl groups are, for example, alkenyl groups such as vinyl, 1-propenyl, 2-propenyl (=allyl), 2-butenyl, 3-butenyl, 2-methyl-2-butenyl, 3-methyl-2-butenyl, 5-hexenyl, or 1,3-pentadienyl, or alkynyl groups such as ethynyl, 1-propynyl, 2-propynyl (=propargyl), or 2-butynyl. Alkyl groups can also be unsaturated when they are substituted.

Non-limiting examples of cyclic alkyl groups are cycloalkyl groups containing 3, 4, 5, 6, 7, or 8 ring carbon atoms like cyclopropyl, cyclobutyl, cyclopentyl, cyclohexyl, cycloheptyl, or cyclooctyl, which can also be substituted and/or unsaturated. Unsaturated cyclic alkyl groups and unsaturated cycloalkyl groups such as, for example, cyclopentenyl or cyclohexenyl, can be bonded via any carbon atom. The term alkyl as used herein also comprises cycloalkyl-substituted alkyl groups such as cyclopropylmethyl-, cyclobutylmethyl-, cyclopentylmethyl-, cyclohexylmethyl-, cycloheptylmethyl-, 1-cyclopropylethyl-, 1-cyclobutylethyl-, 1-cyclopentylethyl-, 1-cyclohexylethyl-, 2-cyclopropylethyl-, 2-cyclobutylethyl-, 2-cyclopentylethyl-, 2-cyclohexylethyl-, 3-cyclopropylpropyl-, 3-cyclobutylpropyl-, 3-cyclopentylpropyl-, and others, in which groups the cycloalkyl subgroup as well as acyclic subgroup can be unsaturated and/or substituted.

Of course, a cyclic alkyl group has to contain at least three carbon atoms, and an unsaturated alkyl group has to contain at least two carbon atoms. Thus, a group like $(C_1-C_8)$-alkyl is to be understood as comprising, among others, saturated acyclic $(C_1-C_8)$-alkyl, $(C_3-C_8)$-cycloalkyl, cycloalkyl-alkyl- groups like $(C_3-C_7)$-cycloalkyl-$(C_1-C_3)$-alkyl-wherein the total number of carbon atoms can range from 4 to 8, and unsaturated $(C_2-C_8)$-alkyl like $(C_2-C_8)$-alkenyl or $(C_2-C_8)$-alkynyl. Similarly, a group like $(C_1-C_4)$-alkyl is to be understood as comprising, among others, saturated acyclic $(C_1-C_4)$-alkyl, $(C_3-C_4)$-cycloalkyl, cyclopropylmethyl- and unsaturated $(C_2-C_4$-alkyl like $(C_2-C_4)$-alkenyl or $(C_2-C_4)$-alkynyl.

Unless stated otherwise, in one embodiment of the invention the term alkyl comprises acyclic saturated hydrocarbon residues which have from one to six carbon atoms and which can be linear or branched. A particular group of saturated acyclic alkyl groups is formed by $(C_1-C_4)$-alkyl groups like methyl, ethyl, n-propyl, isopropyl, n-butyl, isobutyl, sec-butyl and tert-butyl.

The above statements relating to alkyl groups do not only apply to monovalent residues but correspondingly to divalent and polyvalent residues like alkanediyl groups, alkylene groups or polymethylene groups, some examples of which are methylene, 1,2-ethylene (=ethane-1,2-diyl), 1,1-ethylene (=1-methyl-methylene), 1-isobutyl-methylene, 1,3-propylene, 2,2-dimethyl-1,3-propylene, 1,4-butylene, but-2-en-1,4-diyl, 1,2-cyclopropylene, 1,2-cyclohexylene, 1,3-cyclohexylene, and 1,4-cyclohexylene.

Examples of $(C_1-C_4)$-alkoxy-$(C_2-C_4)$-alkoxy- groups are 2-methoxyethoxy-, 2-ethoxyethoxy-, 2-isopropoxyethoxy-, 3-methoxypropoxy-, and 4-ethoxybutoxy-.

The term aryl refers to a monocyclic or polycyclic hydrocarbon residue in which residue at least one carbocyclic ring is present which has a conjugated pi electron system, i.e., which is an aromatic ring, and which residue is attached via a carbon atom contained in a ring which has a conjugated pi electron system. In a $(C_6-C_{14})$-aryl group from 6 to 14 ring carbon atoms are present. Examples of $(C_6-C_{14})$-aryl groups are phenyl, naphthyl, biphenylyl, fluorenyl, anthracenyl, indenyl, indanyl, 1,2,3,4-tetrahydronaphthyl or 2,3,4,5-tetrahydro-1H-benzocycloheptenyl. Examples of $(C_6-C_{10})$-aryl groups are phenyl, naphthyl, indenyl, indanyl or 1,2,3,4-tetrahydronaphthyl. Unless stated otherwise, and irrespective of any specific substituents bonded to aryl groups which are indicated in the definition of the compounds of the formula I, aryl groups, for example phenyl, naphthyl or fluorenyl, can in general be unsubstituted or substituted by one or more, for example one, two, three, or four, identical or different substituents, for example by the substituents listed below.

Aryl groups can be bonded via any desired position in an aromatic ring. In substituted aryl groups the substituents can be located in any desired position. In monosubstituted phenyl groups the substituent can be located in the 2-position, the 3-position or the 4-position, such as in the 3-position or the 4-position. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position. Naphthyl groups can be 1-naphthyl (=naphthalen-1-yl) and 2-naphthyl (=naphthalen-2-yl). In substituted naphthyl groups the substituents can be located in any positions, for example in monosubstituted 1-naphthyl groups in the 2-, 3-, 4-, 5-, 6-, 7-, or 8-position and in monosubstituted 2-naphthyl groups in the 1-, 3-, 4-, 5-, 6-, 7-, or 8-position. 1,2,3,4-Tetrahydronaphthyl, when attached via a carbon atom in the aromatic ring and comprised by the term aryl, can be 1,2,3,4-tetrahydronaphthalen-5-yl or 1,2,3,4-tetrahydronaphthalen-6-yl. Biphenylyl groups can be biphenyl-2-yl, biphenyl-3-yl or biphenyl-4-yl. Fluorenyl groups, when comprised by the term aryl, can be bonded via the 1-, 2-, 3-, or 4-position, otherwise via the 1-, 2-, 3-, 4-, or 9-position. In one embodiment of the invention, in monosubstituted fluorenyl groups bonded via the 9-position, the substituent can be present in the 1-, 2-, 3-, or 4-position.

The above statements relating to aryl groups correspondingly apply to divalent and polyvalent groups derived from aryl groups, e.g. to arylene groups like phenylene which can be unsubstituted or substituted 1,2-phenylene, 1,3-phenylene or 1,4-phenylene, or naphthylene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl, or 2,7-naphthalenediyl. The above statements also correspondingly apply to the aryl subgroup in arylalkyl- groups. Examples of arylalkyl- groups, which can also be unsubstituted or substituted in the aryl subgroup as well as in the alkyl subgroup, are benzyl, 1-phenylethyl, 2-phenylethyl, 1-phenylpropyl, 2-phenylpropyl, 3-phenylpropyl, 1-phenylbutyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, and 9-fluorenylmethyl. All the above explanations also apply to aromatic rings which may be condensed (or fused) to a ring formed by the groups $R^4$ and $R^5$ and the carbon atom to which these groups are attached.

The Het group comprises groups containing 3, 4, 5, 6, 7, 8, 9, or 10 ring atoms in the parent monocyclic or bicyclic heterocyclic ring system. In monocyclic Het groups the heterocyclic ring may comprise a 3-membered, 4-membered, 5-membered, 6-membered or 7-membered ring, such as a 5-membered or 6-membered ring. In bicyclic Het groups two fused rings may be present, one of which is a 5-membered ring or 6-membered heterocyclic ring and the other of which is a 5-membered or 6-membered heterocyclic or carbocyclic ring. For example, a bicyclic ring Het may contain 8, 9 or 10 ring atoms, for example, 9 or 10 ring atoms.

Het comprises saturated heterocyclic ring systems which do not contain any double bonds within the rings, as well as unsaturated heterocyclic ring systems including mono-unsaturated and poly-unsaturated heterocyclic ring systems which contain one or more, for example one, two, three, four, or five, double bonds within the rings provided that the resulting system is stable. Unsaturated rings may be partially unsaturated or non-aromatic, or they may be aromatic and thus may contain double bonds arranged in such a manner that a conjugated pi electron system results. Aromatic rings in a Het group may be 5-membered or 6-membered rings. For example, aromatic groups in a Het group contain 5 to 10 ring atoms. Aromatic rings in a Het group thus comprise 5-membered and 6-membered monocyclic heterocycles and bicyclic heterocycles composed of two 5-membered rings, one 5-membered ring and one 6-membered ring, or two 6-membered rings. In bicyclic aromatic groups in a Het group one or both rings may contain heteroatoms. Aromatic Het groups may also be referred to by the customary term heteroaryl for which all the definitions and explanations above and below relating to Het correspondingly apply. These explanations relating to the saturation/unsaturation in heterocyclic ring systems representing the Het group corresponding apply to any other heterocyclic ring system that can be present in a compound of the formula I, for example to a ring formed by $R^4$ and $R^5$ together with the carbon atom to which these groups are bonded, and the ring systems that may be condensed to this ring.

In a Het group and any other heterocyclic group, for example, 1 or 2 identical or different ring heteroatoms selected from nitrogen, oxygen and sulfur atoms may be present. In general, the ring heteroatoms can be present in any desired combination and in any desired positions with respect to each other provided that the resulting heterocyclic system is known in the art and is stable and suitable as a subgroup in a drug substance. Examples of parent structures of heterocycles from which the Het group any other heterocyclic groups can be derived are aziridine, oxirane, azetidine, pyrrole, furan, thiophene, dioxole, imidazole, pyrazole, oxazole, isoxazole, thiazole, isothiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, and pyridopyrimidines, and others, as well as ring systems which result from the listed heterocycles by fusion (or condensation) of a carbocyclic ring, for example benzo-fused, cyclopenta-fused, cyclohexa-fused or cyclohepta-fused derivatives of these heterocycles.

The fact that many of the before-listed names of heterocycles are the chemical names of unsaturated or aromatic ring systems does not imply that the Het groups and other heterocyclic groups could only be derived from the respective unsaturated ring system. The names here only serve to describe the ring system with respect to ring size and the number of the heteroatoms and their relative positions. As explained above, for example a Het group can be saturated or partially unsaturated or aromatic, and can thus be derived not only from the before-listed heterocycles themselves but also from all of their partially or completely hydrogenated analogues as well as from their more highly unsaturated analogues, if applicable. As examples of completely or partially hydrogenated analogues of the before-listed heterocycles from which a Het group and any other heterocyclic group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazole, 1,3-oxazolidine, 4,5-dihydro-1,3-thiazole, 1,3-thiazolidine, perhydro-1,4-dioxine (=1,4-dioxane), piperazine, perhydro-1,4-oxazine (=morpholine), 2,3-dihydrobenzo[1,4]dioxine (=1,4-benzodioxane), 3,4-dihydro-2H-benzo[1,4]oxazine, perhydro-1,4-thiazine (=thiomorpholine), perhydroazepine, indoline, isoindoline, 1,2,3,4-tetrahydroquinoline, and 1,2,3,4-tetrahydroisoquinoline, and others.

The Het group and any other heterocyclic group may be bonded via any ring carbon atom, and in the case of nitrogen heterocycles via any suitable ring nitrogen atom, if applicable. Thus, for example, a pyrrolyl group can be pyrrol-1-yl, pyrrol-2-yl or pyrrol-3-yl, a pyrrolidinyl group can be pyrrolidin-1-yl (=pyrrolidino), pyrrolidin-2-yl or pyrrolidin-3-yl, a pyridinyl group can be pyridin-2-yl, pyridin-3-yl or pyridin-4-yl, a piperidinyl group can be piperidin-1-yl (=piperidino), piperidin-2-yl, piperidin-3-yl or piperidin-3-yl. Furyl can be furan-2-yl or fur-3-yl, thienyl can be thiophen-2-yl or thiophen-3-yl, imidazolyl can be imidazol-1-yl, imidazol-2-yl, imidazol-4-yl, or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl, or 1,3-thiazol-5-yl, pyrimidinyl can be pyrimidin-2-yl, pyrimidin-4-yl (=pyrimidin-6-yl) or pyrimidin-5-yl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl, or indol-7-yl. Similarly benzimidazolyl, benzoxazolyl and benzothiazolyl groups can be bonded via the 2-position and via any of the positions 4, 5, 6, and 7, and in the case of benzimidazolyl, also via the 1-position. Quinolinyl can be quinolin-2-yl, quinolin-3-yl, quinolin-4-yl, quinolin-5-yl, quinolin-6-yl, quinolin-7-yl, or quinolin-8-yl, isoqinolinyl can be isoquinolin-1-yl, isoquinolin-3-yl, isoquinolin-4-yl, isoquinolin-5-yl, isoquinolin-6-yl, isoquinolin-7-yl, or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents in aryl groups, Het groups or any other heterocyclic groups which are indicated in the definition of the compounds of the formula I, aryl groups, Het groups and other heterocyclic groups can be unsubstituted or substituted on ring carbon atoms with one or more, for example one, two, three, four or five, identical or different substituents like $(C_1-C_4)$-alkyl, $(C_1-C_4)$-alkoxy, $(C_1-C_4)$-alkylthio, halogen, nitro, amino, $(C_1-C_4)$-alkylamino, di-$((C_1-C_4)$-alkyl)amino, $((C_1-C_4)$-alkyl)carbonylamino such as, for example, acetylamino, trifluoromethyl, trifluoromethoxy, hydroxy, oxo, hydroxymethyl, methylenedioxy, ethylenedioxy, formyl, acetyl, cyano, methylsulfonyl, optionally substituted phenyl, optionally substituted phenoxy, benzyl optionally substituted in the phenyl group, benzyloxy optionally substituted in the phenyl group, and others. The substituents can be present in any desired position provided that a stable molecule results. An oxo substituent (=O) can of course not be present in an aromatic ring, but can be present if the Het group or any other heterocyclic or carbocyclic group is saturated or partially unsaturated. Examples of oxo-substituted heterocyclic groups are 4H-benzo[1,4]oxazin-3-one, 3H-isobenzofuran-1-one, benzo[1,4]dioxin-2-one, chroman-2-one, and others. Examples of the group Het-oxy-, i.e. the group Het-O—, are pyridinyloxy including pyridin-3-yloxy and pyridin4-yloxy, pyrimidinyloxy including pyrimidin-2-yloxy, piperidinyloxy including piperidin-3-yloxy and piperidin-4-yloxy, and pyrrolidin-3-yloxy. In some embodiments of the invention, not more than two nitro groups are present in the compounds of the formula I.

Further, unless stated otherwise, and irrespective of any specific substituents in Het groups or any other heterocyclic groups which are indicated in the definition of the compounds of the formula I, Het groups and other heterocyclic groups can on each suitable ring nitrogen atom independently of one another be unsubstituted, i.e. carry a hydrogen atom, or be substituted, for example, by $(C_1-C_8)$-alkyl, for example $(C_1-C_4)$-alkyl such as methyl or ethyl, optionally substituted phenyl, phenyl-$(C_1-C_4)$-alkyl-, for example benzyl, optionally substituted in the phenyl group, hydroxy-$(C_2-C_4)$-alkyl- such as, for example 2-hydroxyethyl, acetyl or another acyl group, methylsulfonyl or another sulfonyl group, etc. Another group that may occur as a substituent on a suitable ring nitrogen atom is the acetimino group $CH_3$—$C(=NH)$—. Suitable nitrogen heterocycles can also be present as N-oxides or as quaternary salts. Ring sulfur atoms can be oxidized to the sulfoxide or to the sulfone. Thus, for example, a tetrahydrothienyl residue may be present as S,S-dioxotetrahydrothienyl residue or a thiomorpholinyl residue like thiomorpholin-4-yl may be present as 1-oxo-thiomorpholin-4-yl or 1,1-dioxo-thiomorpholin-4-yl.

The explanations relating to the Het group correspondingly apply to divalent and polyvalent Het groups including divalent and polyvalent heteroaromatic groups which may be bonded via any ring carbon atoms and in the case of nitrogen heterocycles via any carbon atoms and any suitable ring nitrogen atoms or via any suitable ring nitrogen atoms. For example, a pyridinediyl group can be pyridin-2,3-diyl, pyridin-2,4-diyl, pyridin-2,5-diyl, pyridin-2,6-diyl, pyridin-3,4-diyl, or pyridin-3,5-diyl, a piperidinediyl group can be, among others, piperidin-1,2-diyl, piperidin-1,3-diyl, piperidin-1,4-diyl, piperidin-2,3-diyl, piperidin-2,4-diyl, or piperidin-3,5-diyl, a piperazinediyl group can be, among others, piperazin-1,3-diyl, piperazin-1,4-diyl, piperazin-2,3-diyl, piperazin-2,5-diyl, and others. The above statements also correspondingly apply to the Het subgroup in the groups Het-alkyl-. Examples of such groups Het-alkyl- which can also be unsubstituted or substituted in the Het subgroup as well as in the alkyl subgroup, are (pyridin-2-yl)-methyl, (pyridin-3-yl)-methyl, (pyridin-4-yl)-methyl, 2-(pyridin-2-yl)-ethyl, 2-(pyridin-3-yl)-ethyl, and 2-(pyridin-4-yl)-ethyl.

Halogen is fluorine, chlorine, bromine or iodine, in some embodiments being fluorine, chlorine or bromine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I, for example the form in which instead of the group $R^1$—NH—$C(=NH)$— depicted in formula I the tautomeric group $R^1$—N=C(—$NH_2$)— is present.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The choice of incorporating into a compound of the formula I a building block with R configuration or S configuration, or in the case of an amino acid unit present in a compound of the formula I of incorporating a building block designated as D-amino acid or L-amino acid, can depend, for example, on the desired characteristics of the compound of the formula I. For example, the incorporation of a D-amino acid building block can confer increased stability in vitro or in vivo. The incorporation of a D-amino acid building block also can achieve a desired increase or decrease in the pharmacological activity of the compound. In some cases it can be desirable to allow the compound to remain active for only a short period of time. In such cases, the incorporation of an L-amino acid building block into the compound can allow endogenous peptidases in an individual to digest the compound in vivo, thereby limiting the individual's exposure to the active compound. A similar effect may also be observed in the compounds of the invention by changing the configuration in another building block from S configuration to R configuration or vice versa. By taking into consideration the medical needs one skilled in the art can determine the desirable characteristics, for example a favorable stereochemistry, of the required compound of the invention.

Physiologically tolerable salts of the compounds of formula I are nontoxic salts that are physiologically acceptable, such as pharmaceutically utilizable salts. Such salts of compounds of the formula I containing acidic groups, for example a carboxy group COOH, are, for example, alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or amidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. The present invention also includes acid addition salts of compounds of the formula I which contain, for example, two basic groups with one acid equivalent or with two acid equivalents.

Salts of compounds of the formula I can be obtained by customary methods known to those skilled in the art, for example by combining a compound of the formula I with an inorganic or organic acid or base in a solvent or diluent, or from other salts by cation exchange or anion exchange. The present invention also includes all salts of the compounds of the formula I which, because of low physiological tolerability, are not directly suitable for use in pharmaceuticals but are suitable, for example, as intermediates for carrying out further chemical modifications of the compounds of the formula I or as starting materials for the preparation of physiologically tolerable salts.

The anions of the mentioned acids that may be present in acid addition salts of the compounds of the formula I, are also examples of anions that may be present in the compounds of the formula I if they contain one or more positively charged groups like trialkylammonio-substituents, i.e. groups of the formula $(alkyl)_3N^+$ bonded via the positively charged nitrogen atom, which groups may represent $R^{10}$, or quaternized ring nitrogen atoms in heterocyclic groups. In general a compound of the formula I contains one or more physiologically tolerable anions or anion equivalents as counterions if it contains one or more permanently positively charged groups like trialkylammonio. Compounds of the formula I which simultaneously contain a basic group or a positively charged group and an acidic group, for example an amidino group and a carboxy group, can also be present as zwitterions (or betaines or inner salts) which are likewise included in the present invention.

The present invention furthermore includes all solvates of compounds of the formula I, for example hydrates or adducts with alcohols. The invention also includes derivatives and modifications of the compounds of the formula I, for example protected forms, prodrugs, i.e. compounds which in vitro do not necessarily exhibit pharmacological activity but which in vivo are converted into active compounds, and other physiologically tolerable derivatives including esters and amides of acid groups, as well as active metabolites of the compounds of the formula I.

The structural elements in the compounds of formula I have the following example denotations which they can have independently of the denotations of other elements.

The number m, i.e. the number of halogen atoms that are present as substituents on the phenylene group depicted in formula I, in some embodiments can be 0, 1 or 2, such as 0 or 1, or 0. Those positions of the phenylene group depicted in formula I which do not carry a substituent A carry hydrogen atoms. Thus, if m is zero and accordingly no substituent A is present, said phenylene group carries four hydrogen atoms. If 1, 2, 3, or 4 substituents A are present, said phenylene group carries 3, 2, 1, or 0 hydrogen atoms, respectively.

The number n, i.e. the number of the $CH_2$ groups in the polymethylene chain connecting the nitrogen of the amido group C(=O)—NH depicted in formula I and the group —$CR^3R^4R^5$, is 0 or 1 in some embodiments, for example, 0. Thus, the group —$(CH_2)_n$— in some embodiments can be a direct bond or the group —$CH_2$—. For example, the group —$(CH_2)_n$— can be a direct bond, i.e. the nitrogen atom of the amido group —C(=O)—NH— is directly bonded to the —$CR^3R^4R^5$ group.

The substituents A, which in general can be identical or different, are, in some embodiments, selected from fluorine, chlorine and bromine, such as from fluorine and chlorine. As outlined above with respect to aryl groups and phenyl groups in general, the substituents A can be present in any desired position on the phenyl ring to which they are bonded. If only one substituent A is present, it can be located in the 2-position or in the 3-position with respect to the (thio)urea group, if two substituents A are present, they can be located in the 2,3-position, 2,5-position, 2,6-position and 3,5-position with respect to the (thio)urea group.

In some embodiments of the invention, X can be oxygen.

$R^1$ can be hydrogen, hydroxy or $(C_1-C_{12})$-alkoxycarbonyl- in some embodiments. In other embodiments it can be hydrogen, hydroxy or $(C_1-C_4)$-alkoxycarbonyl-, such as hydrogen or hydroxy, and such as hydrogen.

If an aryl group present in a group $R^1$ is substituted by one or more identical or different substituents selected from $(C_1-C_{12})$-alkyl, halogen and $(C_1-C_{12})$-alkoxy, it can be substituted by 1, 2 or 3, such as by 1 or 2, identical or different substituents, for example by one substituent. An alkyl group or alkoxy group present in a substituent in a group $R^1$ can be a $(C_1-C_4)$-alkyl group or $(C_1-C_4)$-alkoxy group, respectively.

In some embodiments of the invention, $R^2$ can be selected from hydrogen, $(C_1-C_{12})$-alkyl, $(C_6-C_{14})$-aryl, and $(C_6-C_{14})$-aryl-$(C_1-C_4)$-alkyl-, such as from hydrogen, $(C_1-C_8)$-alkyl, $(C_6-C_{10})$-aryl and $(C_6-C_{10})$-aryl-$(C_1-C_4)$-alkyl-. In other embodiments $R^2$ is hydrogen.

In some embodiments, $R^3$ can be hydrogen.

If a group $R^4$ or $R^5$ or a cyclic group formed by $R^4$ and $R^5$ together with the carbon atom to which they are bonded is substituted by one or more substituents $R^{10}$, it may carry, for example, 1, 2, 3, 4, or 5 identical or different substituents $R^{10}$, such as 1, 2, 3, or 4, or such as 1, 2, or 3, or such as 1 or 2, identical or different substituents $R^{10}$.

In some embodiments of the invention, $R^4$ can be selected from $(C_1-C_8)$-alkyl, $(C_6-C_{10})$-aryl, $(C_6-C_{10})$-aryl-$(C_1-C_4)$-alkyl-, Het, and Het-$(C_1-C_4)$-alkyl-, where the alkyl, aryl and Het groups are unsubstituted or substituted by one or more identical or different substituents $R^{10}$. In other embodiments, $R^4$ is $(C_6-C_{10})$-aryl or Het, such as $(C_6-C_{10})$-aryl, for example phenyl, where the aryl, Het and phenyl groups are unsubstituted or substituted by one or more identical or different substituents $R^{10}$.

In some embodiments $R^5$ can be selected from hydrogen, $(C_1-C_{12})$-alkyl, $(C_6-C_{14})$-aryl, $(C_6-C_{14})$-aryl-$(C_1-C_4)$-alkyl-, Het, and Het-$(C_1-C_4)$-alkyl-, such as from hydrogen, $(C_1-C_8)$-alkyl, $(C_6-C_{10})$-aryl, $(C_6-C_{10})$-aryl-$(C_1-C_4)$-alkyl-, Het, and Het-$(C_1-C_4)$-alkyl-, or such as from hydrogen, $(C_1-C_8)$-alkyl, $(C_6-C_{10})$-aryl and $(C_6-C_{10})$-aryl-$(C_1-C_4)$-alkyl-, or such as from hydrogen, $(C_1-C_4)$-alkyl and phenyl, or such as from $(C_1-C_4)$-alkyl and phenyl, for example from methyl, ethyl and phenyl, where the alkyl, aryl, phenyl, and Het groups are unsubstituted or substituted by one or more identical or different substituents $R^{10}$. Moreover, in some embodiments, $R^5$ is $(C_1-C_4)$-alkyl, for example methyl or ethyl.

The saturated or unsaturated carbocyclic or heterocyclic ring that may be formed by $R^4$ and $R^5$ together with the carbon atom to which they are bonded can contain 3, 4, 5, 6, 7, or 8 ring atoms. In some embodiments of the invention, such a ring is a saturated or unsaturated 5-membered or 6-membered carbocyclic or heterocyclic ring. The one or two ring systems that may be condensed (or fused) to bonds in a ring formed by $R^4$ and $R^5$ together with the carbon atom to which they are bonded, can be identical or different monocyclic or bicyclic saturated or unsaturated ring systems composed of 5-membered and 6-membered rings. In some embodiments, the rings condensed to the ring formed by $R^4$ and $R^5$ together with the carbon atom to which they are bonded are identical or different carbocyclic or heterocyclic aromatic ring systems, for example aromatic ring systems selected from benzene and naphthalene. In other embodiments, one or two benzene rings may be condensed to a ring formed by $R^4$ and $R^5$ together with the carbon atom to which they are bonded. Examples of ring systems formed by $R^4$ and $R^5$ together with the carbon atom to which they are bonded are cyclopropane, cyclopentane, cyclohexane, cycloheptane, tetrahydrofuran, tetrahydropyran, pyrrolidine, piperidine, perhydroazepine, indane, indene, dihydronaphthalene, tetrahydronaphthalene, octahydronaphthalene, decahydronaphthalene, fluorene, benzoindane, acenaphthene, 9,10-dihydroanthracene, chromane, chromene, isochromane, tetrahydroquinoline, tetrahydroisoquinoline, and others, which may all be unsubstituted or substituted by one or more identical or different substituents $R^{10}$.

In some embodiments of the invention, $R^6$ can be hydrogen or hydroxy, for example hydrogen.

In one embodiment of the invention an aryl group or Het group, such as an aryl group, representing $R^4$ or $R^5$ or present in the aryl or Het part of an arylalkyl- or Het-alkyl-group representing $R^4$ or $R^5$, for example such a group representing $R^4$, is substituted by one or more identical or different substituents $R^{10}$. Within said embodiment of the invention a subgroup of compounds is formed by compounds in which the substituent $R^{10}$ or the substituents $R^{10}$ on aryl groups or Het groups representing $R^4$ or $R^5$ or present in the aryl or Het part of an arylalkyl- or Het-alkyl-group representing $R^4$ or $R^5$ are selected from halogen, for example fluorine, chlorine and bromine, $(C_1-C_8)$-alkyl, $(C_1-C_8)$-alkoxy, $(C_6-C_{10})$-aryloxy-, and $(C_6-C_{10})$-aryl-$(C_1-C_4)$-alkoxy-, where each of the aryl groups in a group $R^{10}$ is unsubstituted or substituted as defined above. Another subgroup of compounds within said embodiment of the invention is formed by compounds in which on aryl groups or Het groups representing $R^4$ or $R^5$ or present in the aryl or Het part of an arylalkyl- or Het-alkyl- group representing $R^4$ or $R^5$ one substituent $R^{10}$ is present which is selected from $(C_1-C_8)$-alkylcarbonylamino-, $(C_6-C_{10})$-arylcarbonylamino-, $(C_6-C_{10})$-aryl-$(C_1-C_4)$-alkylcarbonylamino-, Het-carbonylamino-, Het-$(C_1-C_4)$-alkylcarbonylamino-, $(C_1-C_8)$-alkylaminocarbonyl-, $(C_6-C_{10})$-arylaminocarbonyl-, $(C_6-C_{10})$-aryl-$(C_1-C_4)$-alkylaminocarbonyl-, Het-aminocarbonyl-, Het-$(C_1-C_4)$-alkylaminocarbonyl-, $(C_1-C_8)$-alkylaminosulfonyl-, $(C_6-C_{10})$-arylaminosulfonyl-, $(C_6-C_{10})$-aryl-$(C_1-C_4)$-alkylaminosulfonyl-, Het-aminosulfonyl-, Het-$(C_1-C_4)$-alkylaminosulfonyl-, $(C_1-C_8)$-alkylsulfonylamino-, $(C_6-C_{10})$-arylsulfonylamino-, $(C_6-C_{10})$-aryl-$(C_1-C_4)$-alkylsulfonylamino-, Het-sulfonylamino-, and Het-$(C_1-C_4)$-alkylsulfonylamino-, and zero, one or two identical or different substituents $R^{10}$ are present which are selected from halogen, for example fluorine, chlorine and bromine, $(C_1-C_8)$-alkyl, $(C_1-C_8)$-alkoxy, $(C_6-C_{10})$-aryloxy- and $(C_6-C_{10})$-aryl-$(C_1-C_4)$-alkoxy-, where each of the aryl groups and Het groups in a group $R^{10}$ is unsubstituted or substituted as defined above. Further subgroups of compounds within said embodiment of the invention are formed by compounds in which on aryl groups or Het groups representing $R^4$ or $R^5$ or present in the aryl or Het part of an arylalkyl- or Het-alkyl- group representing $R^4$ or $R^5$ one substituent $R^{10}$ is present which is selected either from $(C_1-C_8)$-alkylcarbonylamino-, $(C_6-C_{10})$-arylcarbonylamino-, $(C_6-C_{10})$-aryl-$(C_1-C_4)$-alkylcarbonylamino-, Het-carbonylamino-, and Het-$(C_1-C_4)$-alkylcarbonylamino-, or from $(C_1-C_8)$-alkylaminocarbonyl-, $(C_6-C_{10})$-arylaminocarbonyl-, $(C_6-C_{10})$-aryl-$(C_1-C_4)$-alkylaminocarbonyl-, Het-aminocarbonyl-, and Het-$(C_1-C_4)$-alkylaminocarbonyl-, or from $(C_1-C_8)$-alkylaminosulfonyl-, $(C_6-C_{10})$-arylaminosulfonyl-, $(C_6-C_{10})$-aryl-$(C_1-C_4)$-alkylaminosulfonyl-, Het-aminosulfonyl-, and Het-$(C_1-C_4)$-alkylaminosulfonyl-, or from $(C_1-C_8)$-alkylsulfonylamino-, $(C_6-C_{10})$-arylsulfonylamino-, $(C_6-C_{10})$-aryl-$(C_1-C_4)$-alkylsulfonylamino-, Het-sulfonylamino-, and Het-$(C_1-C_4)$-alkylsulfonylamino-, and in each of these cases zero, one or two identical or different substituents $R^{10}$ are present which are selected from halogen, for example fluorine, chlorine and bromine, $(C_1-C_8)$-alkyl, $(C_1-C_8)$-alkoxy, $(C_6-C_{10})$-aryloxy- and $(C_6-C_{10})$-aryl-$(C_1-C_4)$-alkoxy-, where each of the aryl groups and Het groups in a group $R^{10}$ is unsubstituted or substituted as defined above.

The invention comprises all compounds of the formula I in which one or more of the groups are defined as in any of the embodiments described above or have one or more of the specific denotations listed in their respective definitions or in the general explanations on the respective groups, all combinations of such specific denotations being a subject of the present invention. Also, all of these compounds of the formula I are a subject of the present invention in all their stereoisomeric forms and mixtures thereof in any ratio, and in the form of their physiologically tolerable salts. For example, a group of compounds is formed by compounds of the formula I in which n is 0;

$R^3$ is hydrogen;

$R^5$ is methyl, ethyl or phenyl where the phenyl group is unsubstituted or substituted by one or more identical or different substituents $R^{10}$; and m, A, X, $R^1$, $R^2$, $R^4$, $R^6$ and $R^{10}$ are as defined in their general definitions or in any of the embodiments described above, in all their stereoisomeric forms and mixtures thereof in any ratio, and their physiologically tolerable salts.

Another group of compounds is formed by compounds of the formula I in which n is 0;

m is 0 or 1;

$R^2$ is hydrogen;

$R^3$ is hydrogen;

$R^5$ is methyl, ethyl or phenyl where the phenyl group is unsubstituted or substituted by one or more identical or different substituents $R^{10}$;

$R^6$ is hydrogen or hydroxy;

X is oxygen; and

A, $R^1$, $R^4$ and $R^{10}$ are as defined in their general definitions or in any of the embodiments described above, in all their stereoisomeric forms and mixtures thereof in any ratio, and their physiologically tolerable salts.

Yet another group of compounds of the invention is formed by compounds of the formula I, wherein m is 0, 1, 2, 3 or 4;

n is 0, 1, 2 or 3;

A is halogen;

X is sulfur or oxygen;

$R^1$ is selected from hydrogen, hydroxy, $(C_1-C_{12})$-alkoxycarbonyl-, $(C_6-C_{14})$-aryl-$(C_1-C_4)$-alkoxycarbonyl- and $(C_6-Ci_4)$-aryloxycarbonyl-, where each of the aryl groups is unsubstituted or substituted by one or more identical or different substituents selected from $(C_1-C_{12})$-alkyl, halogen and $(C_1-C_{12})$-alkoxy;

$R^2$ is selected from hydrogen, $(C_1-C_{12})$-alkyl, $(C_6-C_{14})$-aryl, $(C_6-C_{14})$-aryl-$(C_1-C_4)$-alkyl-, $R^{20}$—$(C_1-C_{12})$-alkyl-, $R^{20}$-$(C_6-C_{14})$-aryl-, and $R^{20}$—$(C_6-C_{14})$-aryl-$(C_1-C_4)$-alkyl-, where $R^{20}$ is selected from hydroxycarbonyl-, $(C_1-C_{12})$-alkoxycarbonyl- and $(C_6-C_{14})$-aryl-$(C_1-C_4)$-alkoxycarbonyl-;

$R^3$ is selected from hydrogen, cyano, hydroxy and $(C_1-C_{12})$-alkyl;

$R^4$ is selected from $(C_1-C_{12})$-alkyl, $(C_6-C_{14})$-aryl, $(C_6-C_{14})$-aryl-$(C_1-C_4)$-alkyl-, Het and Het-$(C_1-C_4)$-alkyl-, where the alkyl, aryl and Het groups are unsubstituted or substituted by one or more identical or different substituents $R^{10}$;

$R^5$ is selected from hydrogen, $(C_1-C_{12})$-alkyl, $(C_6-C_{14})$-aryl, $(C_6-C_{14})$-aryl-$(C_1-C_4)$-alkyl-, Het, Het-$(C_1-C_4)$-alkyl-, $(C_6-C_{14})$-aryl-$(C_1-C_4)$-alkyl-aminocarbonyl- and Het-$(C_1-C_4)$-alkyl-aminocarbonyl-, where the alkyl, aryl and Het groups are unsubstituted or substituted by one or more identical or different substituents $R^{10}$; or R$^4$ and R$^5$ together with the carbon atom to which they are bonded form a saturated or unsaturated 3-membered to 8-membered ring which is a carbocyclic ring or a heterocyclic ring containing 1, 2 or 3 identical or different ring heteroatoms selected from nitrogen, oxygen and sulfur, and which can be condensed to one or two saturated or unsaturated carbocyclic ring systems or heterocyclic ring systems containing 5 to 10 ring atoms of which 1, 2 or 3 can be identical or different ring heteroatoms selected from nitrogen, oxygen and sulfur, where the resulting R$^4$(R$^5$)C group is unsubstituted or substituted by one or more identical or different substituents R$^{10}$;

R$^6$ is selected from hydrogen, hydroxy, (C$_1$–C$_8$)-alkoxy, and (C$_6$–C$_{14}$)-aryl-(C$_1$–C$_4$)-alkoxy-;

R$^{10}$ is selected from (C$_1$–C$_{12}$)-alkyl, phenyl-(C$_1$–C$_4$)-alkyl-, (C$_1$–C$_8$)-alkoxy, phenyl-(C$_1$–C$_4$)-alkoxy-, phenoxy-, phenyl, Het, trifluoromethoxy, trifluoromethyl, halogen, oxo, hydroxy, amino, (C$_1$–C$_{12}$)-alkylcarbonylamino-, (C$_1$–C$_8$)-alkylcarbonyl-, cyano, nitro, amidino, acetimino, tri-((C$_1$–C$_4$)-alkyl)ammonio-, (C$_1$–C$_8$)-alkylamino-, di-((C$_1$–C$_8$)-alkyl)amino-, hydroxycarbonylmethoxy-, (C$_1$–C$_8$)-alkylsulfonyl-, (C$_1$–C$_8$)-alkylsulfonylamino-, phenylsulfonylamino- and phenylsulfonyl-, where the Het group and each of the phenyl groups contained in R$^{10}$ is unsubstituted or substituted by one or more identical or different substituents selected from halogen, nitro, oxo, hydroxy, (C$_1$–C$_8$)-alkyl, (C$_1$–C$_8$)-alkoxy, trifluoromethyl, cyano, trifluoromethoxy, (C$_1$–C$_8$)-alkylsulfonyl-, amino, (C$_1$–C$_8$)-alkylamino-, di-((C$_1$–C$_8$)-alkyl)amino-, (C$_1$–C$_8$)-alkylcarbonylamino- and (C$_1$–C$_8$)-alkylcarbonyl-;

Het is a residue of a saturated or unsaturated monocyclic or bicyclic, 3-membered to 10-membered heterocyclic ring system containing 1, 2 or 3 identical or different ring heteroatoms selected from nitrogen, oxygen and sulfur;

in all their stereoisomeric forms and mixtures thereof in any ratio, and their physiologically tolerable salts.

In a further embodiment of the invention, chiral centers in the compounds of formula I independently of one another are present in uniform or substantially uniform configuration.

The present invention also relates to processes of preparation by which the compounds of the formula I are obtainable. The compounds of the formula I can generally be prepared by linkage of two or more fragments (or building blocks) which can be derived retrosynthetically from the formula I. In the preparation of the compounds of the formula I it can generally be advantageous or necessary in the course of the synthesis to introduce functional groups which could lead to undesired reactions or side reactions in a synthesis step in the form of precursors which are later converted into the desired functional groups. As examples of precursor groups cyano groups may be mentioned which may later be converted into amidino groups, or nitro groups which may be converted into amino groups. Protecting groups (or blocking groups) that may be present on functional groups include allyl, tert-butyl, benzyl, allyloxycarbonyl (Alloc), tert-butoxycarbonyl (Boc), benzyloxycarbonyl (Z), and 9-fluorenylmethoxycarbonyl (Fmoc) as protecting groups for hydroxy, carboxylic acid, amino, and amidino groups.

In the preparation of the compounds of the formula I, building blocks can be connected by performing one or more condensation reactions and/or addition reactions such as amide couplings and (thio)urea formations, i.e. by forming an amide bond between a carboxylic acid group of one building block and an amino group of another building block, or by establishing a (thio)urea linkage between two amino groups of two building blocks. For example, compounds of the formula I can be prepared by linking the building blocks of the formulae II, III, and IV

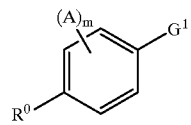

II

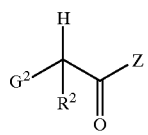

III

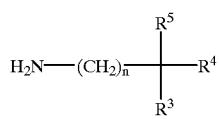

IV by means of forming, in a manner known to those of skill in the art, a (thio)urea bridge between the group G$^1$ depicted in formula II and the group G$^2$ depicted in formula III, and by forming, in a manner known to those of skill in the art, an amide bond between the carboxylic acid derivative group COZ depicted in formula III and the NH$_2$ group depicted in formula IV.

In the compounds of the formulae II, III and IV the groups and numbers m, n, A, R$^2$, R$^3$, R$^4$ and R$^5$ are as defined above. R$^0$ is the amidino group R$^1$NH—C(=NH)— wherein R$^1$ is defined as above, or a protected form thereof or a precursor group thereof, for example a cyano group which is later converted into the group R$^1$NHC(=NH)— present in the final compounds of formula I. In general, in addition to the denotations of the groups and substituents given above, in the compounds of the formulae II, III and IV, functional groups can also be present in the form of precursor groups which are later converted into the groups present in the compounds of the formula I, or can be present in protected form.

One of the groups G$^1$ and G$^2$ is a free amino group, i.e. an NH$_2$ group in the case of G$^1$ and an NHR$^6$ group in the case of G$^2$, and the other is an amino group suitably functionalized for the formation of a (thio)urea bridge, or is converted into such a functionalized group, for example an iso(thio)cyanato group or a (C$_1$–C$_6$)-alkoxycarbonylamino group or a trichloromethylcarbonylamino group or an azolyl-N-(thio)carbonylamino group such as an imidazol-1-yl(thio)carbonylamino group, where the functionalized group G$^2$ contains the group R$^6$ or a protected form or a precursor group of the group R$^6$. The group Z in the compounds of the formula III is hydroxy or a nucleophilically substitutable leaving group, i.e. the group COZ in the compounds of the formula III is a carboxylic acid group COOH or an activated derivative of a carboxylic acid such as, for example, an acid chloride, an ester like a (C$_1$–C$_4$)-alkyl ester or an activated ester, or a mixed anhydride.

The starting compounds of the formulae II, III and IV and other compounds which are employed in the synthesis of the compounds of formula I for introducing certain structural units, are commercially available or can be readily prepared from commercially available compounds by or analogously to procedures described below or in the literature which is readily available to those skilled in the art.

For the preparation of the compounds of formula I first the compounds of the formulae II and III may be linked and the resulting intermediate product then be condensed with a compound of the formula IV to give a compound of the formula I. Just so, first the compounds of the formulae III and IV may be condensed and the resulting intermediate product then be linked to a compound of the formula II to give a compound of the formula I. After any such reaction step in the course of such syntheses protecting and deprotecting steps and conversions of precursor groups into the desired final groups may be carried out and further modifications may be made.

The (thio)urea bridge between the building blocks for formulae II and III can be established, for example, by first converting in a compound of the formula II an amino group ($NH_2$ group) representing $G^1$ into a functionalized amino group like an iso(thio)cyanato group by means of (thio)phosgene or a phosgene equivalent like triphosgene, or a ($C_1$–$C_6$)-alkoxycarbonylamino group by means of a ($C_1$–$C_6$)-alkyl chloroformate such as ethyl chloroformate or isobutylchloroformate, or an imidazol-1-yl(thio)carbonylamino group by means of N,N'-(thio)carbonyldiimidazole, or a trichloromethylcarbonylamino group by means of trichloroacetyl chloride. The resulting intermediate is then reacted with a compound of the formula III in which $G^2$ is a free $NHR^6$ group which adds to the iso(thio)cyanato group or replaces the imidazolyl group, alkoxy group or trichloromethyl group, respectively. Alternatively, first in a compound of the formula III an amino group ($NHR^6$ group) representing $G^2$ can be functionalized to give an iso(thio)cyanato group, ($C_1$–$C_6$)-alkoxycarbonylamino group, imidazol-1-yl(thio)carbonyl group or trichloromethylcarbonylamino group, and the resulting intermediate is then reacted with a compound of the formula II in which $G^1$ is a free $NH_2$ group. The conversion of an amino group into an iso(thio)cyanato group, ($C_1$–$C_6$)-alkoxycarbonylamino group, imidazol-1-yl (thio)carbonyl group or trichloromethylcarbonylamino group as well as the subsequent reaction of the intermediate with an amine can be performed according to standard procedures which are well known to those skilled in the art.

Various general methods for the formation of an amide bond that can be employed in the synthesis of the compounds of formula I are just so well known to those skilled in the art, for example from peptide chemistry. An amide coupling step can, for example, be carried out by employing a free carboxylic acid, i.e. a compound of the formula III or an intermediate coupling product in which a group like COZ reacting in that step is a COOH group, activating that carboxylic acid group, such as in situ, by means of a customary coupling reagent such as a carbodiimide like dicyclohexylcarbodiimide (DCC) or diisopropylcarbodiimide (DIC), or an N,N'-carbonyldiazole like N,N'-carbonyldiimidazole, or a uronium salt like O-((cyano(ethoxycarbonyl)methylene)-amino)-1,1,3,3-tetramethyluronium tetrafluoroborate (TOTU) or O-(7-azabenzotriazol-1-yl)-1,1,3,3-tetramethyluronium hexafluorophosphate (HATU), or a chloroformic acid ester like ethyl chloroformate or isobutyl chloroformate, or tosyl chloride, or propylphosphonic acid anhydride, or others, and then reacting the activated carboxylic acid derivative with an amino compound of the formula IV. An amide bond can also be formed by reacting an amino compound with a carboxylic acid halide, such as a carboxylic acid chloride, which can be prepared in a separate step or in situ from a carboxylic acid and, for example, thionyl chloride, or an carboxylic acid ester or thioester, for example a methyl ester, ethyl ester, phenyl ester, nitrophenyl ester, pentafluorophenyl ester, methylthio ester, phenylthio ester or pyridin-2-ylthio ester, i.e. with a compound of the formula III or with an intermediate coupling product in which a group like Z is chlorine, methoxy, ethoxy, optionally substituted phenoxy, methylthio, phenylthio, or pyridin-2-ylthio.

The activation reactions and coupling reactions are usually performed in the presence of an inert solvent (or diluent), for example in the presence of an aprotic solvent like dimethylformamide (DMF), tetrahydrofuran (THF), dimethylsulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and may be, for example, from about −20° C. to about the boiling temperature of the solvent or diluent. Also depending on the specific process, it may be necessary or advantageous to add in a suitable amount of one or more auxiliary agents, for example a base like a tertiary amine, such as triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, J. March, Advanced Organic Chemistry, 4th ed., John Wiley & Sons, 1992; or Houben-Weyl, Methoden der organischen Chemie [Methods of Organic Chemistry], Georg Thieme Verlag.

Protective groups that may still be present in the products obtained in the coupling reaction are then removed by standard procedures. For example, tert-butyl protecting groups can be cleaved off with trifluoroacetic acid. Accordingly, a tert-butoxycarbonyl-substituted amidino group or amino group which is a protected form of an amidino group or amino group, can be deprotected, i.e. converted into the amidino group or amino group, by treatment with trifluoroacetic acid. As already explained, functional groups can also be generated after the coupling reaction from suitable precursor groups. In addition, a conversion into a physiologically tolerable salt or a prodrug of a compound of the formula I can then be carried out by known processes.

As examples of the introduction of specific functional groups, procedures for the introduction of amidino groups, i.e. the group $H_2N$—C(=NH)— also designated as amino-imino-methyl- group or carbamimidoyl group, may be explained which groups may also represent the group $R^{10}$, for example. Amidines can be prepared from cyano compounds by addition of an alcohol under acidic anhydrous conditions, for example in methanol or ethanol saturated with hydrogen chloride, and subsequent ammonolysis. A further method of preparing amidines is the addition of hydrogen sulfide to the cyano group, followed by methylation of the resulting thioamide and subsequent reaction with ammonia. Another method is the addition of hydroxylamine to the cyano group which leads to a hydroxyamidino group. If desired the N—O bond in the hydroxyamidine can be cleaved, for example by catalytic hydrogenation, to give the amidine.

In general, a reaction mixture containing a final compound of the formula I or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

The reactions described above and below that are carried out in the syntheses of the compounds of the formula I can generally be carried out according to the methods of conventional solution phase chemistry.

The compounds of the present invention inhibit the activity of the blood coagulation enzyme factor VIIa. For example, they are specific inhibitors of factor VIIa. As used herein, the term specific when used in reference to the inhibition of factor VIIa activity means that a compound of the formula I can inhibit factor VIIa activity without substantially inhibiting the activity of other specified proteases involved in the blood coagulation and/or the fibrinolysis pathway including, for example, factor Xa, plasmin and thrombin (using the same concentration of the inhibitor). The compounds of the invention inhibit factor VIIa catalytic activity either directly, within the prothrombinase complex or as a soluble subunit, or indirectly, by inhibiting the assembly of factor VIIa into the prothrombinase complex.

Because of their factor VIIa inhibitory activity the compounds of the formula I are useful pharmacologically active compounds which are suitable, for example, for influencing blood coagulation (or blood clotting) and fibrinolysis and for the treatment, including therapy and prophylaxis, of diseases such as, for example, cardiovascular disorders, thromboembolic diseases or restenoses. The compounds of the formula I and their physiologically tolerable salts and their prodrugs can be administered to animals, for example to mammals, such as humans, as pharmaceuticals for therapy or prophylaxis. They can be administered on their own, or in mixtures with one another or in the form of pharmaceutical preparations which permit enteral or parenteral administration and which contain, as active constituent, an effective amount of at least one compound of the formula I and/or its physiologically tolerable salts and/or its prodrugs and a pharmaceutically acceptable carrier.

The present invention therefore also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of factor VIIa or for influencing blood coagulation or fibrinolysis or for the treatment, including therapy and prophylaxis, of the diseases mentioned above or below, for example for the production of pharmaceuticals for the treatment of cardiovascular disorders, thromboembolic diseases or restenoses. The invention also relates to the use of the compounds of the formula I and/or their physiologically tolerable salts and/or their prodrugs for the inhibition of factor VIIa or for influencing blood coagulation or fibrinolysis or for the treatment of the diseases mentioned above or below, for example for use in the treatment, including therapy and prophylaxis, of cardiovascular disorders, thromboembolic diseases or restenoses, and to methods of treatment aiming at such purposes including methods for said therapies and prophylaxes. The present invention furthermore relates to pharmaceutical preparations (or pharmaceutical compositions) which contain an effective amount of at least one compound of the formula I and/or its physiologically tolerable salts and/or its prodrugs and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula I and/or its (their) physiologically tolerable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, and natural and hardened oils, and others. Suitable carrier substances for the production of solutions, for example injection solutions, or of emulsions or syrups are, for example, water, saline, alcohols, glycerol, polyols, sucrose, invert sugar, glucose, vegetable oils, and others. Suitable carrier substances for microcapsules, implants or rods are, for example, copolymers of glycolic acid and lactic acid. The pharmaceutical preparations normally contain about 0.5 to about 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 to about 1000 mg, for example from about 1 to about 500 mg, per unit, but depending on the type of the pharmaceutical preparation it may also be higher.

In addition to the active ingredients of the formula I and/or their physiologically acceptable salts and/or prodrugs and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents, and antioxidants. They can also contain two or more compounds of the formula I and/or their physiologically tolerable salts and/or their prodrugs. In case a pharmaceutical preparation contains two or more compounds of the formula I the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or its physiologically tolerable salts and/or its prodrugs, the pharmaceutical preparations can also contain one or more other therapeutically or prophylactically active ingredients.

As inhibitors of factor VIIa the compounds of the formula I and their physiologically tolerable salts and their prodrugs are generally suitable for the therapy and prophylaxis of conditions in which the activity of factor VIIa plays a role or has an undesired extent, or which can favorably be influenced by inhibiting factor VIIa or decreasing its activity, or for the prevention, alleviation or cure of which an inhibition of factor VIIa or a decrease in its activity is desired by the physician. As inhibition of factor VIIa influences blood coagulation and fibrinolysis the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus is the reduction or inhibition of unwanted blood clotting, such as in an individual, by administering an effective amount of a compound I or a physiologically tolerable salt or a prodrug thereof, as well as pharmaceutical preparations therefor.

Conditions in which a compound of the formula I and/or a physiologically tolerable salt thereof and/or a prodrug thereof can be favorably used include, for example, cardiovascular disorders, thromboembolic diseases or complications associated, for example, with infection or surgery. The compounds of the present invention can also be used to reduce an inflammatory response. Examples of specific disorders for the treatment, including therapy and prophylaxis, of which the compounds of the formula I can be used are coronary heart disease, myocardial infarction, angina pectoris, vascular restenosis, for example restenosis following angioplasty like PTCA, adult respiratory distress syndrome, multi-organ failure, stroke, and disseminated intravascular clotting disorder. Examples of related complications associated with surgery are thromboses like deep vein and proximal vein thrombosis which can occur following surgery. In view of their pharmacological activity the compounds of the invention can replace other anticoagulant agents such as heparin. The use of a compound of the invention can result, for example, in a cost saving as compared to other anticoagulants.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, such as from 0.1 to about 50 mg/kg, or such as from about 0.1 to about 10 mg/kg, (in each case in mg per kg of body weight). The daily dose can be divided, for example in the case of the administration of relatively large amounts, into several, for example 2, 3 or 4, part administrations. As usual, depending on individual behavior, it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I or its salts can be used for diagnostic purposes, for example in in vitro diagnoses, and as an auxiliary or tool in biochemical investigations. For example, a compound of the formula I can be used in an assay to identify the presence of factor VIIa or to isolate factor VIIa in a substantially purified form. A compound of the invention can be labeled, for example, with a radioisotope and the labeled compound bound to factor VIIa is then detected using a routine method useful for detecting the particular label. Thus, a compound of the formula I or a salt thereof can be used advantageously as a probe to detect the location or amount of factor VIIa activity in vivo, in vitro or ex vivo.

Furthermore, the compounds of the formula I can be used as synthesis intermediates for the preparation of other compounds, for example of other pharmaceutically active ingredients, which are obtainable from the compounds of the formula I, for example by introduction of substituents or modification of functional groups.

It is understood that modifications that do not substantially affect the activity of the various embodiments of this invention are included within the invention disclosed herein. Accordingly, the following examples are intended to illustrate but not limit the present invention.

EXAMPLES

| Abbreviations | |
|---|---|
| DCC | N,N'-Dicyclohexylcarbodiimide |
| DIEA | N,N-Diisopropyl-N-ethylamine |
| DMF | N,N-Dimethylformamide |
| DMSO | Dimethylsulfoxide |
| NEM | N-Ethylmorpholine |
| HOBt | N-Hydroxybenzotriazole |
| THF | Tetrahydrofuran |
| TFA | Trifluoroacetic acid |
| TOTU | O-(Cyano(ethoxycarbonyl)methyleneamino)-1,1,3,3-tetramethyluronium tetrafluoroborate |

When in the final step of the synthesis of a compound an acid such as trifluoroacetic acid or acetic acid was used, for example when trifluoroacetic acid was employed to remove a tert-butyl group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt.

Example 1

(S)-N-(4-Carbamimidoylbenzyl)-2-[3-(4-carbamimidoylphenyl)ureido]propionamide

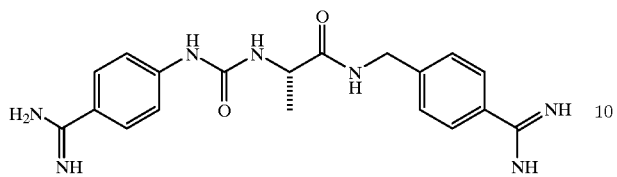

1a. (S)-2-[3-(4-Cyanophenyl)ureido]propionic Acid Ethyl Ester

A solution of 4-aminobenzonitrile (2.3 g, 0.0195 mol) and N,N'-carbonyldiimidazole (3.5 g, 0.332 mol) in DMF (20 ml) was heated at 80° C. for 7 hours (h). A solution of L-alanine ethyl ester (3 g, 0.0195 mol) in DMF (15 ml) was added and stirring was continued for 3 days (d) at 80° C. Water (300 ml) was added and the precipitate was filtered off (giving 750 mg of the dimer as side product). The solution was extracted with ethyl acetate to give 3 g of the title compound which contained the corresponding acid as side product. MS (mass spectrometry) peak was at 262.1 (M+1)$^+$.

1b. (S)-2-[3-(4-Cyanophenyl)ureido]propionic Acid

A solution of the compound of example 1a) (3 g, 0.0115 mol) in methanol (60 ml) and NaOH (2 N, 5.75 ml) was stirred for 16 h at room temperature. The solvent was removed and water was added. An aqueous solution of HCl (1 N) was added and the precipitate was separated to give 0.95 g (37%) of the title compound. MS 234.2 (M+1)$^+$ 1c. (S)-N-(4-Cyanobenzyl)-2-[3-(4-cyanophenyl)ureido]propionamide To a solution of the compound of example 1b) (0.222 g, 0.953 mmol), p-toluenesulfonic acid salt of 4-aminomethylbenzonitrile (0.290 g, 0.953 mmol), NEM (0.12 ml) and HOBt (0.129 g, 0.953 mmol) in DMF (20 ml) DCC (0.179 g, 0.953 mmol) was added at 0C. The solution was stirred for 1 h at 3 to 10° C. and 12 h at room temperature. The precipitate was filtered off. The solvent was removed and the residue was dissolved in ethyl acetate (60 ml), washed with saturated aqueous NaHCO$_3$ solution (2×20 ml) and dried (MgSO$_4$). The solvent was removed to give 0.46 g of the title compound which was used without further purification. MS 348.1 (M+1)$^+$ 1d. (S)-N-(4-Carbamimidoylbenzyl)-2-[3-(4-carbamimidoylphenyl)ureido]propionamide A solution of the compound of example 1c) (0.380 g, 1.10 mmol) in pyridine/triethylamine (5 ml, 1:1) was saturated with gaseous hydrogen sulfide (N$_2$). After 48 h at room temperature the solvent was removed and a solution of methyl iodide (0.60 ml, 11 mmol) in acetone (2 ml) was added. After stirring at room temperature for 48 h the solvent was removed and a solution of ammonium acetate (0.85 mg, 11 mmol) in methanol (10 ml) and acetic acid (0.5 ml) was added and the mixture was stirred for 48 h at room temperature. The solvent was removed and the residue was purified by HPLC to give 24 mg (36%) of the title compound. MS 382.3 (M+1)$^+$; MS 191.6 (½ (M+2)$^{2+}$)

Example 2

2-[3-(4-Carbamimidoylphenyl)ureido]-N-(4-dimethylaminobenzyl)-3-phenylpropionamide

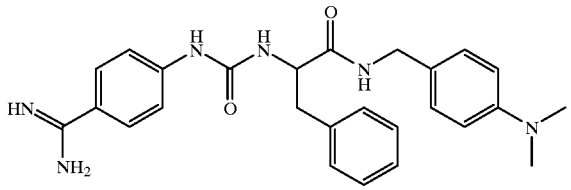

2a. 3-Phenyl-2-[3-(4-cyanophenyl)ureido]propionic Acid Ethyl Ester

To a solution of 2-isocyanato-3-phenylpropionic acid ethyl ester (6 g, 27.37 mmol) in DMF (50 ml) was added a solution of 4-aminobenzonitrile (3.23 g, 27.37 mmol) in DMF (30 ml) at 3° C. during 20 min. Stirring was continued for 7 d at room temperature, and additional 2-isocyanato-3-phenylpropionic acid ethyl ester (2.86 g) was added successively. The solvent was removed and the residue dissolved in ethyl acetate (100 ml), washed with water (20 ml), saturated aqueous KHSO$_4$/K$_2$SO$_4$ solution (1:1, 2×20 ml) and with saturated aqueous NaCl solution (4×90 ml). The organic phase was dried (MgSO$_4$), filtered and evaporated to give 12.20 g of the title compound which was used without further purification. MS 338.3 (M+1)$^+$ 2b. 2-[3-(4-Carbamimidoylphenyl)ureido]-3-phenylpropionic Acid Ethyl Ester A solution of the compound of example 2a) (12.04 g) in ethanol (100 ml) was saturated with dried gaseous HCl at 5 to 15° C. After 48 h at room temperature the solvent was removed. A saturated solution of ammonia in ethanol (19 ml, 57.1 mmol) was added to the residue and the mixture was stirred for 48 h at room temperature. The mixture was filtered off and ethyl acetate (180 ml) was added to the solution. The precipitate was filtered to give 7.5 g (67%) of the title compound. MS 355.2 (M+1)$^+$ 2c. 2-{3-[4-(tert-Butoxycarbonylamino-tert-butoxycarbonylimino-methyl)phenyl]ureido}-3-phenylpropionic Acid Ethyl Ester A mixture of the compound of example 2b) (7.5 g, 19.19 mmol), NaHCO$_3$ (4.84 g, 57.56 mmol) and di-tert-butyl dicarbonate (8.37 g, 38.37 mmol) in ethanol (100 ml) was stirred at 40° C. After 16 h the inorganic salt was filtered off and the solvent was removed. The residue was dissolved in ethyl acetate (150 ml), washed with water (50 ml), dried (MgSO$_4$), filtered and evaporated to give 8.91 g of the title compound which was used without further purification.

2d. 2-{3-[4-(tert-Butoxycarbonylamino-tert-butoxycarbonylimino-methyl)phenyl]ureido}-3-phenylpropionic Acid Sodium Salt To a solution of the compound of example 2c) (8.91 g) in ethanol (70 ml) was added a solution of NaOH (0.84 g, 21.11 mmol) in water (15 ml). After 7 h at room temperature the solution was concentrated (40 ml), cooled down and the precipitate was filtered off and washed with ethyl acetate (2×15 ml) and ether (20 ml) to give 4.16 g of the title compound. MS 527.3 (M+1)$^+$ 2e. 2-[3-(4-Carbamimidoylphenyl)ureido]-N-(4-dimethylaminobenzyl)-3-phenylpropionamide To a solution of the compound of example 2d) (0.40 g, 0.73 mmol), dihydrochloric acid salt of 4-dimethylaminobenzylamine (0.16 g, 0.73 mmol), and HOBt (0.10 g, 0.73 mmol) in DMF (15 ml) DCC (0.17 g, 0.8 mmol) was added at 0° C. The solution was stirred for 1 h at 3 to 10° C. and 12 h at room temperature. The precipitate was filtered off. The solvent was removed and the residue dissolved in ethyl acetate (40 ml), washed with saturated aqueous NaHCO$_3$ solution (2×5 ml) and with saturated aqueous NaCl solution (2×5 ml). The organic phase was dried (MgSO$_4$) and filtered. The solvent was removed and the residue (0.48 g) was stirred with TFA (1.12 ml, 14.6 mmol) and water (0.17 g) for 24 h at room temperature. Ethyl acetate (20 ml) and n-pentane (20 ml) were added, the mixture was cooled and the precipitate was filtered off to give 138 mg of the title compound. M.p. 147° C. MS 459.3 (M+1)$^+$; MS 230.1 (½ (M+2)$^{2+}$)

Example 3

2-[3-(4-Carbamimidoylphenyl)ureido]-N-(3,4-dichlorobenzyl)acetamide

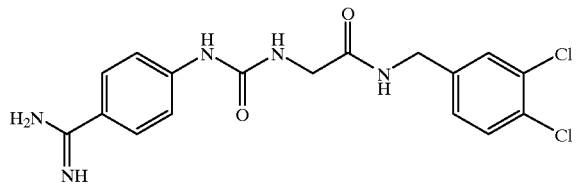

3a. 2-[3-(4-Cyanophenyl)ureido]acetic Acid Ethyl Ester

To a solution of ethoxycarbonylmethyl isocyanate (24.5 ml, 0.212 mol) in DMF (100 ml) a solution of 4-aminobenzonitrile (25 g, 0.212 mol) in DMF (100 ml) was added within 30 min at 0° C. Stirring was continued for 7 d and additional ethoxycarbonylmethyl isocyanate was added periodically (18.5 ml, 0.156 mol). The solvent was removed in vacuo and the residue was stirred in ethyl acetate/diethyl ether. The mixture was filtered to give the title compound (39.12 g, 74%; white solid of m.p. 140–144° C.) which was used without further purification.

3b. 2-[3-(4-Ethoxycarbonimidoylphenyl)ureido]acetic Acid Ethyl Ester

Through a stirred mixture of the compound of example 3a) (22.73 g, 0.0919 mol) in ethanol (500 ml) dry HCl gas was passed through at 0° C. After stirring for 2 d the solid had dissolved. After additional stirring for 2 d a solid precipitated. The solid was filtered off to give 36.99 g (96%) of the title compound (m.p. 140° C. ) which was used without further purification.

3c. 2-[3-(4-Carbamimidoylphenyl)ureido]acetic Acid Ethyl Ester

To a suspension of the compound of example 3b) (18.80 g, 0.057 mol) in ethanol (300 ml) a solution of ammonia in ethanol (150 ml, 0.145 mol) was added. After 30 h the precipitate was filtered and washed with a small amount of ethanol. The residue was stirred with ether and filtered to give 12.33 g (82%) of the title compound. MS 265.1 (M+1)$^+$ 3d. 2-{3-[4-(tert-Butoxycarbonylamino-imino-methyl)phenyl]ureido}acetic Acid Ethyl Ester To a suspension of the compound of example 3c) (42 g, 0.14 mol) and NaHCO$_3$ (35.19 g, 0.42 mol) in ethanol (1.4 l) di-tert-butyl dicarbonate (70.2 g, 0.32 mol) was added successively while the suspension was stirred and heated at 50° C. After 2 d the mixture was filtered and the solvent was removed to a final volume of 100 ml. The precipitate was filtered at 0° C. and the residue washed with diethyl ether. The residue was crystallized (ethanol) to give 18.28 g (36%) of the title compound. M.p. 107–110° C. MS 365.3 (M+1)$^+$ 3e. 2-{3-[4-(tert-Butoxycarbonylamino-imino-methyl)phenyl]ureido}acetic Acid Sodium Salt To a suspension of the compound of example 3d) (2.0 g, 5.49 mmol) in ethanol (50 ml) a solution of NaOH (0.22 g, 5.49 mmol) in water (1 ml) was added. After stirring for 20 h at 20° C. the solvent was removed and the residue freeze dried to give 1.98 g (99%) of the title compound. MS 337.2 (M+1)$^+$ 3f. 2-[3-(4-Carbamimidoylphenyl)ureido]-N-(3,4-dichlorobenzyl)acetamide To a solution of 3,4-dichlorobenzylamine (0.22 ml), the compound of example 3e) (0.6 g, 1.67 mmol) and HOBt (0.23 g, 1.67 mmol) in DMF (30 ml) DCC (0.38 g, 1.84 mmol) was added at 0° C. The solution was stirred for 1 h at 3 to 10° C. and 12 h at room temperature. The precipitate was filtered off. The solvent was removed and the residue dissolved in ethyl acetate (50 ml), washed with saturated aqueous NaHCO$_3$ solution (2×15 ml) and with saturated aqueous NaCl solution (2×40 ml). The organic phase was dried (MgSO$_4$), filtered and evaporated. The residue was dissolved in TFA (2.57 ml) and water (0.38 ml) and stirred for 24 h at room temperature. Dichloromethane (20 ml) and diethyl ether (40 ml) was added and the precipitate was filtered to give 0.59 g (69%) of the title compound. M.p. 221–214° C. MS 394.1 (M+1)$^+$ Example 4

2-[3-(4-Carbamimidoylphenyl)ureido]-N-(4-dimethylaminobenzyl)acetamide

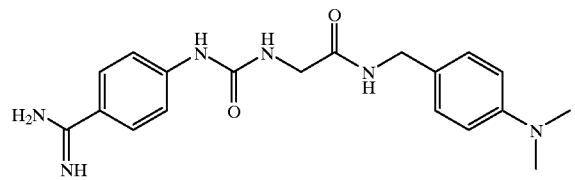

To a solution of 4-dimethylaminobenzylamine (0.42 g, 2.79 mmol), the compound of example 3e) (1 g, 2.79 mmol) and HOBt (0.38 g, 2.79 mmol) in DMF (50 ml) DCC (0.63 g, 3.07 mmol) was added at 0° C. The pH was adjusted to 6 by addition of NEM (0.46 ml). The solution was stirred for 1 h at 3 to 10° C. and 12 h at room temperature. The precipitate was filtered off. The solvent was removed and the residue dissolved in ethyl acetate (110 ml), washed with saturated aqueous NaHCO$_3$ solution (2×20 ml) and with saturated aqueous NaCl solution (3×80 ml). The organic phase was dried (MgSO$_4$), filtered and evaporated. The residue was dissolved in TFA (0.76 ml) and water (0.12 ml) and stirred for 24 h at room temperature. The solvent was removed and the residue was crystallized from water/acetone to give 0.28 g (48%) of the title compound. M.p. 209–214° C. MS 369.2 (M+1)$^+$; MS 185.0 (½ (M+2)$^{2+}$)

Example

N-Benzhydryl-2-[3-(4-carbamimidoylphenyl)ureido]acetamide

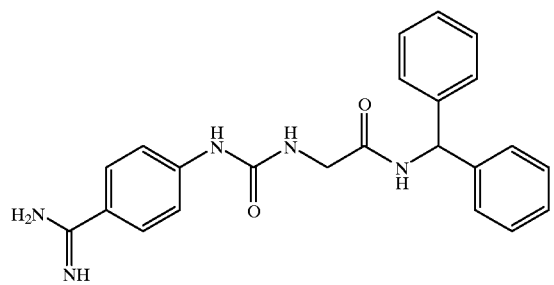

To solution of the compound of example 3e) (0.1 g, 0.3 mmol) in DMF (5 ml) benzhydrylamine (0.051 g, 0.3 mmol), NEM (0.064 g, 0.6 mmol) and TOTU (0.092 g, 0.3 mmol) was added. The solution was stirred for 16 h at room temperature. The precipitate was filtered off. The solvent was removed and the residue was dissolved in aqueous TFA (5 ml, 90%). After stirring at room temperature for 16 h the solvent was removed and the residue was purified by HPLC and freeze-dried to give 0.057 g (37%) of the title compound. MS 402.3 (M+1)$^+$ Analogously to the above examples the following example compounds were prepared which can be named as 2-[3-(4-carbamimidoylphenyl)ureido]-N-(R$^a$-substituted)acetamides (for example, the compound of formula Ia in which R$^a$ is 3-chlorobenzyl can be named as 2-[3-(4-carbamimidoylphenyl)ureido]-N-(3-chlorobenzyl)acetamide).

Example compounds of formula Ia:

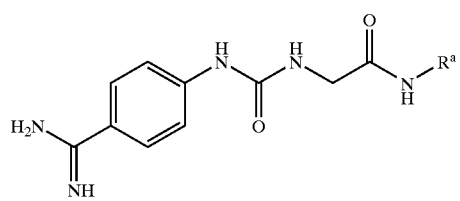

Ia

| Example | R$^a$ in formula Ia | MS |
|---|---|---|
| 6 | 3-chlorobenzyl | 360.2 (M + 1)$^+$ |
| 7 | (S)-1-(1-naphthyl)ethyl | 390.2 (M + 1)$^+$ |
| 8 | 4-chlorobenzyl | 360.2 (M + 1)$^+$ |
| 9 | 1-[4-(2,4-dichlorophenoxy)phenyl]ethyl | 500.2 (M)$^+$ |
| 10 | 2-hydroxy-2-phenylethyl | 356.2 (M − 1)$^+$ |
| 11 | 2-aminoethyl | 279.1 (M + 1)$^+$ |
| 12 | 4-aminobenzyl | 441.4 (M + 1)$^+$ |
| 13 | 4-carbamimidoylbenzyl | 368.6 (M + 1)$^+$ |
|  |  | 185.3 (M + 2)$^{2+}$ |
| 14 | 3,3-diphenylpropyl | 430.3 (M + 1)$^+$ |
| 15 | 1,2-diphenylethyl | 416.2 (M + 1)$^+$ |
| 16 | 3,5-difluorobenzyl | 362.1 (M + 1)$^+$ |
| 17 | 2-chloro-4-fluorobenzyl | 378.1 (M + 1)$^+$ |
| 18 | (S)-1-phenylethyl | 340.2 (M + 1)$^+$ |
| 19 | (R)-1-phenylethyl | 340.2 (M + 1)$^+$ |
| 20 | 2-(4-phenoxyphenyl)ethyl | 432.2 (M + 1)$^+$ |
| 21 | (S)-1-(4-methylphenyl)ethyl | 354.2 (M + 1)$^+$ |
| 22 | 4-hydroxy-3-methoxybenzyl | 372.2 (M + 1)$^+$ |
| 23 | 3-(3-bromophenylsulfonylamino)propyl | 513.1 (M + 1)$^+$ |

Example compounds of formula Ia:

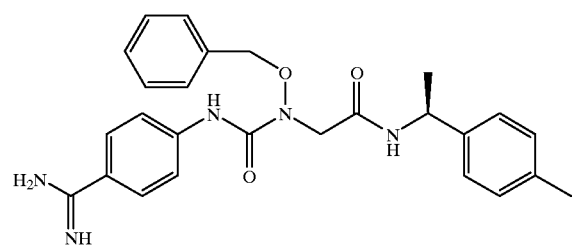

Ia

| Example | R$^a$ in formula Ia | MS |
|---|---|---|
| 24 | 1-(3-bromophenylsulfonyl)piperidin-4-yl | 539.2 (M + 1)$^+$ |
| 25 | 1-(3-hydroxycarbonylmethoxyphenyl)-1-phenylmethyl | 476.1 (M + 1)$^+$ |
| 26 | 4-amino-9H-fluoren-9-yl | 414.1 (M + 1)$^+$ |
| 27 | 1-(4-chlorophenyl)-1-phenylmethyl | 436.16 (M + 1)$^+$ |
| 28 | (S)-1-(4-bromophenyl)ethyl | 418.09 (M + 1)$^+$ |
| 29 | (S)-1-(4-nitrophenyl)ethyl | 385.16 (M + 1)$^+$ |
| 30 | (S)-1-(2-naphthyl)ethyl | 390.20 (M + 1)$^+$ |
| 31 | 1-(1,4-benzodioxan-5-yl)ethyl | 398.18 (M + 1)$^+$ |
| 32 | (S)-1-(3-bromophenyl)ethyl | 418.09 (M + 1)$^+$ |
| 33 | (S)-1-(4-chlorophenyl)ethyl | 374.14 (M + 1)$^+$ |
| 34 | (S)-1-(3-methoxyphenyl)ethyl | 370.19 (M + 1)$^+$ |
| 35 | 1-(4-methylsulfonylphenyl)ethyl | 418.16 (M + 1)$^+$ |
| 36 | 1-[4-(4-methoxyphenoxy)phenyl]ethyl | 462.3 (M + 1)$^+$ |
| 37 | 1-[4-(4-nitrophenoxy)phenyl]ethyl | 477.3 (M + 1)$^+$ |
| 38 | 1-(4-phenoxyphenyl)ethyl | 432.3 (M + 1)$^+$ |
| 39 | 1-(3,4-dichlorophenyl)propyl | 422.2 (M)$^+$ |
| 40 | 1-(4-pyridyl)methyl | 327.1 (M + 1)$^+$ |
|  |  | 164.0 (M + 2)$^{2+}$ |
| 41 | 1-phenyl-1-(4-pyridyl)methyl | 403.19 (M + 1)$^+$ |
| 42 | 1-methyl-1-phenylethyl | 354.19 (M + 1)$^+$ |
| 43 | 1-cyano-1-(4-fluorophenyl)methyl | 369.15 (M + 1)$^+$ |
| 44 | (S)-indan-1-yl | 352.18 (M + 1)$^+$ |
| 45 | (S)-1,2,3,4-tetrahydronaphthalen-1-yl | 366.19 (M + 1)$^+$ |

Example 46

2-[1-Benzyloxy-3-(4-carbamimidoylphenyl)ureido]-N-[(S)-1-(4-methylphenyl)ethyl]acetamide 46a. 2-Benzyloxyaminoacetic Acid Tert-Butyl Ester To a solution of O-benzylhydroxylamine hydrochloride (5 g, 31.3 mmol) in dry DMF (20 ml) was added tert-butyl 2-bromoacetate (4.7 ml, 1 eq.) and potassium carbonate (4.5 g, 1 eq.). The solution was stirred for 16 h at room temperature. The precipitate was filtered off. The solvent was removed, the residue was dissolved in ethyl acetate and extracted with small portions of 1 N HCl, sodium carbonate solution and brine. After drying over sodium sulfate, the solvent was removed to dryness to give 5.86 g (79%) of the title compound as an oil of sufficient purity. MS 182.1 (M+1-tert-butyl)$^+$ 46b. 2-[1-Benzyloxy-3-(4-cyanophenyl)ureido]acetic Acid Tert-Butyl ester To a solution of the compound of example 46a) (2.5 g, 10.5 mmol) in dry THF (20 ml) was added 4-cyanophenylisocyanate (1.5 g, 1 eq.) and the mixture was stirred for 16 h at room temperature. Work-up was done as described for step 40a) to give 4.0 g (99%) of the title compound. MS 326.1 (M+1-tert-butyl)$^+$ 46c. 2-[1-Benzyloxy-3-(4-cyanophenyl)ureido]acetic Acid The compound of example 46b) (2 g, 5.2 mmol) was treated with TFA (15 ml). After 1 h (LC-MS control) TFA was distilled off and the residue was co-evaporated with toluene to give 1.57 g (92%) of the title compound. MS 326.1 (M+1)$^+$ 46d. (S)-2-[1-Benzyloxy-3-(4-cyanophenyl)ureido]-N-(1-(4-methylphenyl)ethyl)acetamide To the compound of example 46c) (1.56 g; 4.83 mmol) in DMF (10 ml)/THF (20 ml), was added (S)-1-(4-methylphenyl)ethylamine (0.68 g, 5 mmol), DIEA (0.83 ml, 1 eq.) and TOTU (1.6 g, 1 eq.). The solution was stirred for 16 h at room temperature. The solvent was removed, the residue dissolved in ethyl acetate and extracted as described for step 46a). The residue was purified by chromatography to give 1.3 g (61%) of the title compound. MS 443.2 (M+1)$^+$ 46e. 2-[1-Benzyloxy-3-(4-carbamimidoylphenyl)ureido]-N-[(S)-1-(4-methylphenyl)ethyl]acetamide The compound of example 46d) (1.5 g, 3.39 mmol) was dissolved in methanol (25 ml). Dry HCl gas was bubbled through the solution at 0° C. with stirring for 4 h, and stirring was continued at room temperature for additional 16 h. Completeness of the imino ester formation was controlled via LC-MS. The solvent was removed and the residue dissolved in dry methanol (20 ml). Ammonium acetate (2.6 g, 34 mmol) was added and the resulting mixture stirred for 40 h at room temperature. The solvent was removed and a small amount of water was added. The product was filtered, washed with water and dried to give 1.02 g (50%) of the title compound. MS 460.20 (M+1)$^+$ Example 47

2-[3-(4-Carbamimidoylphenyl)-1-hydroxyureido]-N-[(S)-1-(4-methylphenyl)ethyl]acetamide

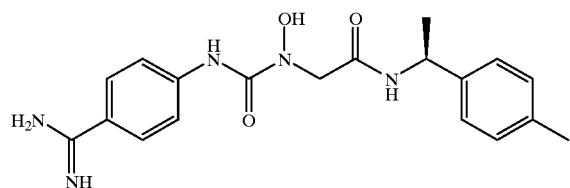

The compound of example 46 (104 mg, 0.2 mmol) was hydrogenated by means of ammonium formate (143 mg) and Pd/C (30 mg; 10%) in methanol (10 ml) at room temperature. After 16 h (LC-MS control) the mixture was filtered off and the solvent was removed. Remaining traces of formate were removed in high vacuo at elevated temperature. 47 mg (57%) of the title compound were obtained. MS 370.10 (M+1)$^+$ Example 48

[Imino-(4-{3-[((S)-1-(4-methylphenyl)ethylcarbamoyl)methyl]ureido}phenyl)-methyl]-carbamic acid 4-methoxyphenyl Ester

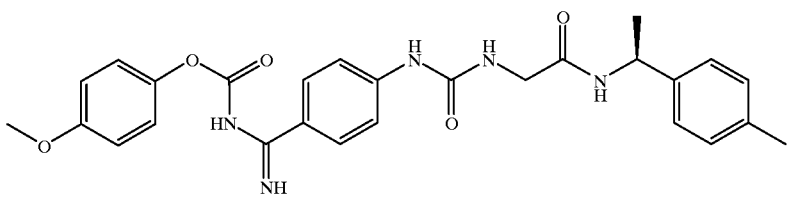

To the compound of example 21 (310 mg, 0.9 mmol) in 1,2-dimethoxyethane (20 ml) were added DIEA (0.34 g, 1.8 mmol) and 4-methoxyphenyl chloroformate (0.344 g, 1.8 mmol). After stirring for 18 h at room temperature the solvent was removed in vacuo and the residue was purified by HPLC to give 63 mg (14%) of the title compound. MS 504.2 (M+1)$^+$.

Example 49

Piperidine-4-carboxylic acid 4-(1-{2-[3-(4-carbamimidoylphenyl)ureido]acetylamino}-ethyl)phenylamide

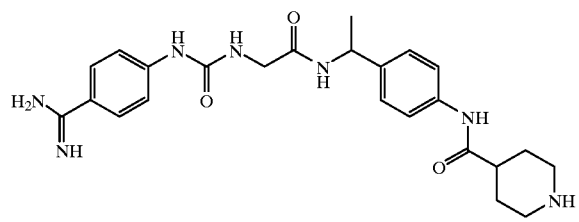

49a. 2-[3-(4-Carbamimidoylphenyl)ureido]acetic Acid

A solution of 2-[3-(4-carbamimidoylphenyl)ureido]acetic acid ethyl ester (24.48 g, 0.0926 mol, compound of example 3c) in ethanol (100 ml) and NaOH (3.705 g, 0.0926 mol, in 5 ml water) was stirred for 22 h at room temperature. The precipitate was filtered off and washed with ethanol to give 24.78 g of the title compound. MS 258.2 (M)$^+$ 49b. 4-(4-Acetylphenylcarbamoyl)piperidine-1-carboxylic Acid Tert-Butyl Ester To a solution of piperidine-1,4-dicarboxylic acid 1-tert-butyl ester (1.69 g, 7.4 mmol) in DMF (20 ml) was added 1-(4-aminophenyl)ethanone (1 g, 7.4 mmol), NEM (0.852 g, 7.4 mmol) and TOTU (2.427 g, 7.4 mmol). The solution was stirred for 16 h at room temperature. The solvent was removed and the residue was dissolved in ethyl acetate (50 ml) and washed with saturated aqueous NaHCO$_3$ solution (5 ml) and HCl (1 N, 10 ml). The organic phase was dried (MgSO$_4$) and filtered. The solvent was removed to give 1.344 g (52%) of the title compound.

33

49c. 4-[4-(1-Aminoethyl)phenylcarbamoyl]piperidine-1-carboxylic Acid Tert-Butyl Ester

A solution of the compound of example 49b) (1.344 g, 3.88 mmol) and ammonium acetate (5.619 g, 72.9 mmol) in methanol (70 ml) was stirred with sodium cyanoborohydride (7.3 ml, 7.29 mmol, 1 M solution in THF) for 7 d. The solvent was removed and the residue was stirred with diethyl ether (25 ml) and water (50 ml). The pH was adjusted to 3–4 by adding concentrated HCl and the phases were separated. The aqueous phase was adjusted to pH>11 by adding KOH, and extracted with ethyl acetate and dried (MgSO$_4$). The solvent was removed to give 1.083 g (80%) of the title compound.

49d. Piperidine-4-carboxylic acid 4-(1-{2-[3-(4-carbamimidoylphenyl)ureido]-acetylamino}ethyl)phenylamide

To a solution of the compound of example 49a) (0.05 g, 0.212 mmol) in DMF (5 ml) was added the compound of example 49c) (0.059 g, 0.17 mmol), NEM (0.024 g, 0.212 mmol) and TOTU (0.065 g, 0.212 mmol). The solution was stirred for 16 h at room temperature. The solvent was removed and the residue was dissolved in TFA (0.5 ml). After 12 h the solvent was removed and the residue was purified by HPLC and freeze-dried to give 59 mg (60%) of the title compound. MS 274.7 (M)$^{2+}$ Analogously to example 49 the following example compounds of formula Ib were prepared which can be named as 2-[3-(4-carbamimidoylphenyl)ureido]-N-{1-[(R$^b$-substituted)phenyl]ethyl}acetamides (for example, the compound of formula Ib in which R$^b$ is 4-(3-methylbenzoylamino) can be named as 2-[3-(4-carbamimidoylphenyl)ureido]-N-{1-[4-(3-methylbenzoylamino)phenyl]ethyl}acetamide).

Example compounds of formula Ib:

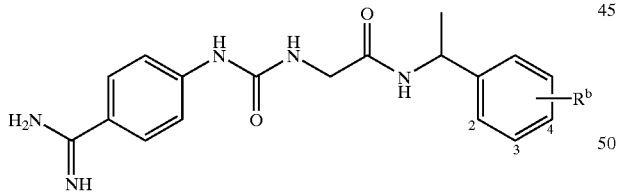

Ib

| Example | R$^b$ in formula Ib | MS |
|---|---|---|
| 50 | 4-(3-methylbenzoylamino) | 473.4 (M + 1)$^+$ |
| 51 | 4-(pyridin-3-carbonylamino) | 460.2 (M + 1)$^+$ |
| 52 | 4-(3-phenoxybenzoylamino) | 551.2 (M + 1)$^+$ |
| 53 | 4-(3-methoxycarbonylbenzoylamino) | 517.4 (M + 1)$^+$ |
| 54 | 4-(4-aminobutyrylamino) | 440.2 (M + 1)$^+$ |
| 55 | 3-(phenylmethanesulfonylamino) | 509.39 (M + 1)$^+$ |
| 56 | 3-(2-acetylamino-4-methyl-[1,3]thiazole-5-sulfonylamino) | 573.37 (M + 1)$^+$ |
| 57 | 3-(propane-2-sulfonylamino) | 461.27 (M + 1)$^+$ |
| 58 | 4-(3-methoxycarbonylphenylcarbamoyl) | 517.41 (M + 1)$^+$ |
| 59 | 4-(3-phenoxyphenylcarbamoyl) | 551.45 (M + 1)$^+$ |

Analogously to examples 1 to 5 the following example compounds were prepared.

34

Example compounds of formula Ia which can be named as 2-[3-(4-carbamimidoylphenyl)ureido]-N-(R$^a$-substituted)acetamides:

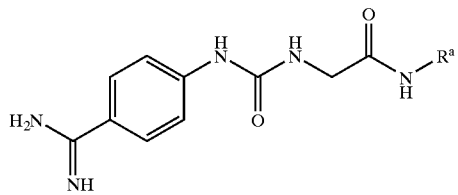

Ia

| Example | R$^a$ in formula Ia | MS |
|---|---|---|
| 60 | 1-(2,4-bis-trifluoromethylphenyl)ethyl | 476.3 (M + 1)$^+$ |
| 61 | 1-(3-oxo-3,4-dihydro-2H-benzo[1,4]oxazin-6-yl)ethyl | 411.3 (M + 1)$^+$ |
| 62 | 1-[4-(3-chlorobenzyloxy)phenyl]ethyl | 480.1 (M + 1)$^+$ |
| 63 | 1-[4-(3-methoxybenzyloxy)phenyl]ethyl | 476.2 (M + 1)$^+$ |
| 64 | 1-(4-benzyloxy-3-methoxycarbonylphenyl)ethyl | 504.2 (M + 1)$^+$ |
| 65 | 1-(4-acetylamino-3-bromophenyl)ethyl | 475.2 (M + 1)$^+$ |
| 66 | 1-(4-ureidophenyl)ethyl | 398.3 (M + 1)$^+$ |
| 67 | 1-[4-(morpholin-4-yl)phenyl]ethyl | 425.4 (M + 1)$^+$ |

Example 68

2-[3-(4-Carbamimidoyl-3-chlorophenyl)ureido]-N-[1-(2,3-dihydrobenzo[1,4]dioxin-6-yl)ethyl]acetamide

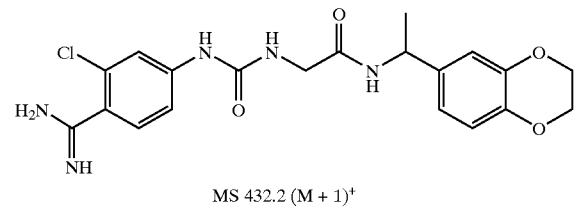

MS 432.2 (M + 1)$^+$

Example 69

N-[(S)-1-(3-Bromophenyl)ethyl]-2-[3-(4-carbamimidoyl-3-fluorophenyl)ureido]-acetamide

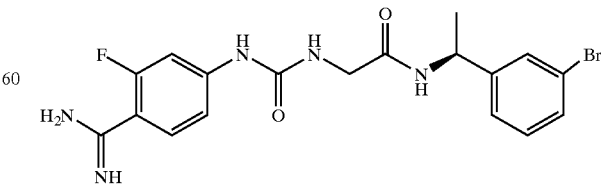

MS 436.0 (M + 1)$^+$

Example 70

(S)-4-[((S)-1-(3-Bromophenyl)ethyl)carbamoyl]-4-[3-(4-carbamimidoylphenyl)ureido]-butyric Acid

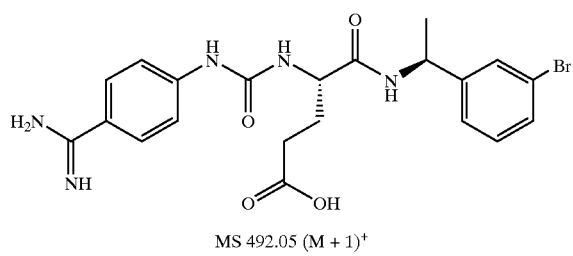

MS 492.05 (M + 1)⁺

Example 71

(S)-2-[3-(4-Carbamimidoylphenyl)ureido]pentanedioic acid 5-amide 1-[(S)-1-(3-bromophenyl)ethylamide]

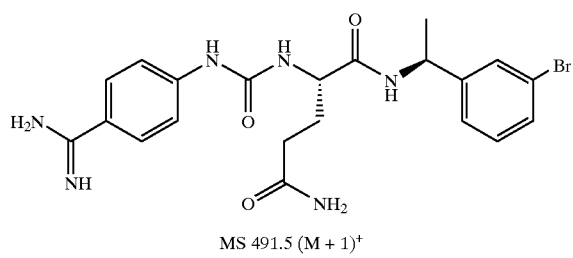

MS 491.5 (M + 1)⁺

Example 72

N-[(S)-1-(3-Bromophenyl)ethyl]-2-[3-(4-carbamimidoylphenyl)ureido]-2-phenylacetamide

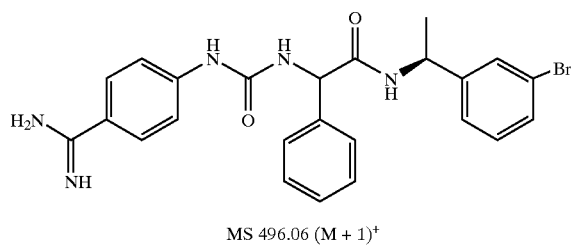

MS 496.06 (M + 1)⁺

Example 73

Pharmacological Testing 73 (I). Enzyme Inhibition

The ability of the compounds of the formula I to inhibit factor VIIa or other enzymes like factor Xa, thrombin, plasmin, or trypsin is assessed by determining the concentration of the compound of the formula I that inhibits enzyme activity by 50%, i.e. the $IC_{50}$ value, which is related to the inhibition constant Ki. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formula I. For calculating the inhibition constant Ki, the $IC_{50}$ value is corrected for competition with substrate using the formula $Ki = IC_{50}/\{1+(\text{substrate concentration}/Km)\}$, wherein Km is the Michaelis-Menten constant (Chen and Prusoff, Biochem. Pharmacol. 22 (1973), 3099–3108; I. H. Segal, Enzyme Kinetics, 1975, John Wiley & Sons, New York, 100–125; which are incorporated herein by reference).

73 (I)a. Factor VIIa (FVIIa) Assay

The inhibitory activity (expressed as inhibition constant Ki(FVIIa)) of the compounds of formula I towards factor VIIa/tissue factor activity was determined using a chromogenic assay essentially as described previously (J. A. Ostrem et al., Biochemistry 37 (1998) 1053–1059 which is incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM $CaCl_2$, 0.05% PEG 8000, pH 8.15). Following a 15 minute preincubation period, the assay was initiated by the addition of 35 µl of the chromogenic substrate S-2288 (D-Ile-Pro-Arg-p-nitroanilide, Pharmacia Hepar Inc., 500 µM final concentration).

The following test results (inhibition constants Ki(FVIIa)) were obtained.

| Example Compound | Ki (FVIIa) (µM) | Example Compound | Ki(FVIIa) (µM) |
|---|---|---|---|
| Example 1 | 14.9 | Example 2 | 20.9 |
| Example 3 | 0.97 | Example 4 | 1.94 |
| Example 5 | 0.73 | Example 6 | 2.17 |
| Example 9 | 0.48 | Example 15 | 6.30 |
| Example 18 | 0.43 | Example 19 | 20.2 |
| Example 21 | 0.13 | Example 30 | 0.026 |
| Example 36 | 0.083 | Example 37 | 0.086 |
| Example 40 | 7.89 | Example 41 | 0.84 |
| Example 42 | 7.62 | Example 43 | 8.47 |
| Example 44 | 1.50 | Example 45 | 1.41 |
| Example 49 | 0.013 | Example 51 | 0.050 |
| Example 52 | 0.012 | Example 54 | 0.047 |
| Example 60 | 0.027 | Example 61 | 0.023 |
| Example 64 | 0.033 | Example 68 | 3.94 |
| Example 69 | 0.116 | Example 70 | 0.539 |

The following tests can serve to investigate the inhibition of selected other coagulation enzymes and other serine proteases by the compounds of formula I and thus to determine their specificity.

73 (I)b. Factor Xa Assay

TBS-PEG buffer (50 mM Tris-Cl, pH 7.8, 200 mM NaCl, 0.05% (w/v) PEG-8000, 0.02% (w/v) $NaN_3$) is used for this assay. The $IC_{50}$ is determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay is performed by pre-incubating the compound of formula I plus enzyme for 10 min. Then the assay is initiated by adding substrate to obtain a final volume of 100 µl. The initial velocity of chromogenic substrate hydrolysis is measured by the change in absorbance at 405 nm using a Bio-tek Instruments kinetic plate reader (Ceres UV900HDi) at 25° C. during the linear portion of the time course (usually 1.5 min after addition of substrate). The enzyme concentration is 0.5 nM and substrate concentration is 140 µM.

73 (I)c. Thrombin Assay

TBS-PEG buffer is used for this assay. The $IC_{50}$ is determined as above for the factor Xa assay, except that the substrate is S-2366 (L-PyroGlu-L-Pro-L-Arg-p-nitroanilide; Kabi) and the enzyme is human thrombin (Enzyme Research Laboratories, Inc.; South Bend, Ind.). The enzyme concentration is 175 μM.

73 (I)d. Plasmin Assay

TBS-PEG buffer is used for this assay. The $IC_{50}$ is determined as described above for the factor Xa assay, except that the substrate is S-2251 (D-Val-L-Leu-L-Lys-p-nitroanilide; Kabi) and the enzyme is human plasmin (Kabi). The enzyme concentration is 5 nM and the substrate concentration is 300 μM.

73 (I)e. Trypsin Assay

TBS-PEG buffer containing 10 mM $CaCl_2$ is used for this assay. The $IC_{50}$ is determined as described above in the factor Xa assay, except that the substrate is BAPNA (benzoyl-L-Arg-p-nitroanilide; Sigma Chemical Co.; St. Louis, Mo.) and the enzyme is bovine pancreatic trypsin (Type XIII, TPCK treated; Sigma). The enzyme concentration is 50 nM and the substrate concentration is 300 μM.

73 (II) Rat Arteriovenous Shunt Model of Thrombosis

The antithrombotic efficacy of the compounds of the invention can be assessed using rat extracorporeal arteriovenous (AV) shunt. The AV shunt circuit consists of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completing the circuit into the left jugular vein. The entire circuit is filled with normal saline prior to insertion.

The test compound is administered by continuous infusion into the tail vein using a syringe pump and butterfly catheter. The compound is administered for 30 min, then the shunt is opened and blood allowed to flow for a period of 15 min (total of 45 min infusion). At the end of the 15 min period, the shunt is clamped and the thread is carefully removed and weighed on an analytical balance. Percent inhibition of thrombus formation is calculated using the thrombus weight obtained from control rats which are infused with saline.

All publications, patents, and patent applications cited herein are incorporated in their entirety by reference.

What is claimed is:

1. A compound of the formula I,

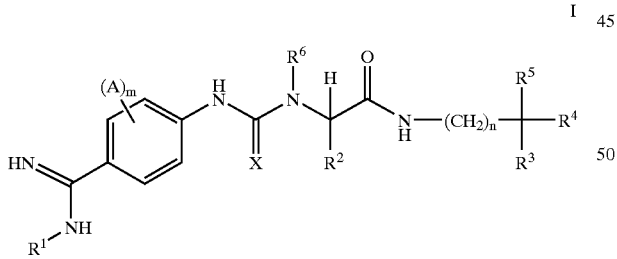

I wherein
m is 0, 1, 2, 3, or 4;
n is 0, 1, 2, or 3;
A is halogen;
X is sulfur or oxygen;
$R^1$ is chosen from hydrogen, hydroxy, $(C_1-C_{12})$-alkoxycarbonyl-, $(C_6-C_{14})$-aryl-$(C_1-C_4)$-alkoxycarbonyl-, and $(C_6-C_{14})$-aryloxycarbonyl-, wherein each of the aryl groups is unsubstituted or substituted by at least one identical or different substituent chosen from $(C_1-C_{12})$-alkyl, halogen and $(C_1-C_{12})$-alkoxy;

$R^2$ is chosen from hydrogen, $(C_1-C_{12})$-alkyl, $(C_6-C_{14})$-aryl, $(C_6-C_{14})$-aryl-$(C_1-C_4)$-alkyl-, $R^{20}$-$(C_6-C_{12})$-alkyl-, $R^{20}$-$(C_1-C_{14})$-aryl-, and $R^{20}$-$(C_6-C_{14})$-aryl-$(C_1-C_4)$-alkyl-, wherein $R^{20}$ is chosen from hydroxycarbonyl-, aminocarbonyl-, $(C_1-C_{12})$-alkoxycarbonyl-, and $(C_6-C_{14})$-aryl-$(C_1-C_4)$-alkoxycarbonyl-;

$R^3$ is chosen from hydrogen, cyano, hydroxy, and $(C_1-C_{12})$-alkyl;

$R^4$ is chosen from $(C_1-C_{12})$-alkyl, $(C_6-C_{14})$,-aryl, $(C_8-C_{14}$-aryl-$(C_1-C_4)$-alkyl-, Het, and Het-$(C_1-C_4)$-alkyl-, wherein the alkyl, aryl and Het groups are unsubstituted or substituted by at least one identical or different substituent $R^{10}$;

$R^5$ is chosen from hydrogen, $(C_1-C_{12})$-alkyl, $(C_6-C_{14})$-aryl, $(C_6-C_{14})$-aryl-$(C_1-C_4)$-alkyl-, Het, Het-$(C_1-C_4)$-alkyl-, $(C_6-C_{14})$-aryl-$(C_1-C_4)$-alkyl-aminocarbonyl-, and Het-$(C_1-C_4)$-alkyl-aminocarbonyl-, wherein the alkyl, aryl and Het groups are unsubstituted or substituted by at least one identical or different substituent $R^{10}$;

or $R^4$ and $R^5$ together with the carbon atom to which they are bonded form a saturated or unsaturated 3-membered to 8-membered ring which is a carbocyclic ring or a heterocyclic ring containing 1, 2 or 3 identical or different ring heteroatoms chosen from nitrogen, oxygen and sulfur, and which is optionally condensed to one or two saturated or unsaturated carbocyclic ring systems or heterocyclic ring systems containing 5 to 10 ring atoms of which 1, 2 or 3 are identical or different ring heteroatoms chosen from nitrogen, oxygen and sulfur, wherein the resulting $R^4(R^5)C$ group is unsubstituted or substituted by at least one identical or different substituent $R^{10}$;

$R^6$ is chosen from hydrogen, hydroxy, $(C_1-C_8)$-alkoxy, and $(C_6-C_{14})$-aryl-$(C_1-C_4)$-alkoxy-;

$R^{10}$ is chosen from $(C_1-C_{12})$-alkyl, $(C_6-C_{14})$-aryl-$(C_1-C_4)$-alkyl-, $(C_1-C_8)$-alkoxy, $(C_1-C_4)$-alkoxy-$(C_2-C_4)$-alkoxy-, $(C_6-C_{14})$-aryl-$(C_1-C_4)$-alkoxy-, $(C_6-C_{14})$-aryloxy-, Het-oxy-, Het-$(C_1-C_4)$-alkoxy-, $(C^6-C_{14})$-aryl, Het, Het-$(C_1-C_4,$-alkyl-, trifluoromethoxy, trifluoromethyl, halogen, oxo, hydroxy, amino, $(C_1-C_{12})$-alkylcarbonylamino-, aminocarbonylamino-, $(C_6-C_{14})$-arylcarbonylamino-, Het-carbonylamino-, $(C_6-C_{14})$-aryl-$(C_1-C_4)$-alkylcarbonylamino-, Het-$(C_1-C_4)$-alkylcarbonylamino-, $(C_1-C_8)$-alkylcarbonyl-, $(C_6-C_{14})$-arylcarbonyl-, $(C_1-C_8)$-alkylaminocarbonyl-, $(C_6-C_{14})$-arylaminocarbonyl-, $(C_6-C_{14}$-aryl-$(C_1-C_4)$-alkylaminocarbonyl-, Het-aminocarbonyl-, Het-$(C_1-C_4)$-alkylaminocarbonyl-, aminocarbonyl-, $(C_1-C_8)$-alkoxycarbonyl-, hydroxycarbonyl-, cyano, nitro, amidino, acetimino, tri-$((C_1-C_4)$-alkyl)ammonio-, $(C_1-C_8)$-alkylamino-, di-$((C_1-C_8)$-alkyl)amino-, hydroxycarbonylmethoxy-, $(C_1-C_8)$-alkylsulfonyl-, $(C_6-C_{14})$-arylsulfonyl-, $(C_1-C_8)$-alkylaminosulfonyl-, $(C_6-C_{14})$-arylaminosulfonyl-, $(C_6-C_{14})$-aryl-$(C_1-C_4)$-alkylaminosulfonyl-, Het-aminosulfonyl, Het-$(C_1-C_4)$-alkylaminosulfonyl-, $(C_1-C_8)$-alkylsulfonylamino-, $(C_6-C_{14})$-arylsulfonylamino-, $(C_6-C_{14})$-aryl-$(C_1-C_4)$-alkylsulfonylamino-, Het-sulfonylamino-, and Het-$(C_1-C_4)$-alkylsulfonylamino-, wherein $(C_1-C_{12})$-alkylcarbonylamino- representing $R^{10}$ is unsubstituted or substituted in the alkyl group by a substituent chosen from amino, hydroxy and $(C_1-C_4)$-alkoxy, and wherein $(C_1-C_{12})$-alkyl and $(C_1-C_8)$-alkoxy representing $R^{10}$ are unsubstituted or substituted by at least one identical or different substituent chosen from $(C_1-C_8)$-alkoxycarbonyl-, hydroxycarbonyl- and aminocarbonyl-, wherein each of the aryl groups and Het group in a group $R^{10}$ is unsubstituted or substituted by at least one identical or different substituent chosen from halogen, nitro, oxo, hydroxy, $(C_1-C_8)$-alkyl, $(C_1-C_8)$-alkoxy, $(C_1-C_4)$-alkoxy-$(C_2-C_4)$-alkoxy-, $(C_6-C_{14})$-aryloxy-, $(C_6-C_{14}$-aryl-$(C_1-C_4)$-alkoxy-, Het-oxy-, Het-$(C_1-C_4)$-alkoxy-, $(C_6-C_{14})$-aryl, $(C_6-C_{14})$-aryl-$(C_1-C_4)$-alkyl-, Het, Het-$(C_1-C_4)$-alkyl-, trifluoromethyl, cyano, trifluoromethoxy, $(C_1-C_8)$-alkylsulfonyl-, $(C_1-C_8)$-alkoxycarbonyl-, hydroxycarbonyl-, aminocarbonyl-, amino, $(C_1-C_8)$-alkylamino-, di-(($C_1-C_8$)-alkyl)amino-, $(C_1-C_8)$-alkylcarbonylamino-, $(C_6-C_{14})$-aryl-$(C_1-C_4)$-alkylcarbonylamino-, $(C_6-C_{14})$-arylcarbonylamino-, Het-carbonylamino-, Het-$(C_1-C_4)$-alkylcarbonylamino-, and $(C_1-C_8)$-alkylcarbonyl-, wherein $(C_1-C_8)$-alkyl and $(C_1-C_8)$-alkoxy representing a substituent on an aryl group or Het group in a group $R^{10}$ are unsubstituted or substituted by at least one identical or different substituent chosen from $(C_1-C_8)$-alkoxycarbonyl-, hydroxycarbonyl- and aminocarbonyl-, with the proviso that, when a substituent $R^{10}$ is bonded to an alkyl group, it cannot be $(C_1-C_8)$-alkoxycarbonyl-, hydroxycarbonyl-, aminocarbonyl-, $(C_1-C_8)$-alkylaminocarbonyl-, or $(C_1-C_8)$-alkylaminosulfonyl-, and that, when a substituent $R^{10}$ is bonded to an alkyl group, it cannot be $(C_1-C_8)$-alkyl which is substituted by at least one identical or different substituent chosen from $(C_1-C_8)$-alkoxycarbonyl-, hydroxycarbonyl- and aminocarbonyl-;

Het is a residue of a saturated or unsaturated monocyclic or bicyclic, 3-membered to 10-membered heterocyclic ring system containing 1, 2 or 3 identical or different ring heteroatoms chosen from nitrogen, oxygen and sulfur;

or a physiologically tolerable salt thereof, in any stereoisomeric form, or a mixture of any such compounds in any ratio.

2. The compound of the formula I as claimed in claim 1, in which X is oxygen, or a physiologically tolerable salt thereof, in any stereoisomeric form, or a mixture of any such compounds in any ratio.

3. The compound of the formula I as claimed in claim 1, in which $R^1$ is chosen from hydrogen, hydroxy and $(C_1-C_4)$-alkoxycarbonyl-, or a physiologically tolerable salt thereof, in any stereoisomeric form, or a mixture of any such compounds in any ratio.

4. The compound of the formula I as claimed in claim 1, in which $R^2$ is hydrogen, or a physiologically tolerable salt thereof, in any stereoisomeric form, or a mixture of any such compounds in any ratio.

5. The compound of the formula I as claimed in claim 1, in which $R^6$ is chosen from hydrogen and hydroxy, or a physiologically tolerable salt thereof, in any stereoisomeric form, or a mixture of any such compounds in any ratio.

6. The compound of the formula I as claimed in claim 1, in which n is 0, $R^3$ is hydrogen and $R^5$ is chosen from methyl, ethyl and phenyl, wherein the phenyl group is unsubstituted or substituted by at least one identical or different substituent $R^{10}$; or a physiologically tolerable salt thereof, in any stereoisomeric form, or a mixture of any such compounds in any ratio.

7. A process for the preparation of at least one compound of formula I as claimed in claim 1, comprising linking the compounds of formulae II, III and IV with formation of a (thio)urea bridge between the groups $G^1$ and $G^2$ in formulae II and III and an amide bond between the COZ group in formula II and the NH2 group In formula IV,

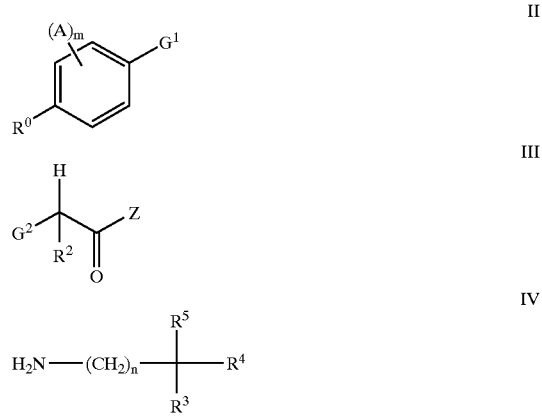

wherein (a) $G^1$ is $NH_2$ and $G^2$ is chosen from iso(thio)cyanato, $(C_1-C_6)$-alkoxycarbonylamino, trichloromethylcarbonylamino, and azolyl-N-(thio)carbonylamino, wherein these groups contain the group $R^6$; or (b) $G^1$ is chosen from iso(thio)cyanato, $(C_1-C_8)$-alkoxycarbonylamino, trichloromethylcarbonylamino, and azolyl-N-(thio)carbonylamino and $G^2$ is $NHR^6$; and Z in the compound of formula III is chosen from hydroxy and a nucleophilically substitutable leaving group; $R^0$ in the compound of formula II is chosen from $R^1NH-C(=NH)$-, a protected form thereof, and a precursor group thereof; and m, n, A, $R^1$, $R^2$, $R^3$; $R^4$, $R^5$ and $R^6$ are defined as in claim 1, but wherein functional groups can also be present in protected form or in the form of precursor groups.

8. A pharmaceutical composition, comprising at least one compound chosen from the compounds of the formula I as claimed in claim 1 and their physiologically tolerable salts, and a pharmaceutically acceptable carrier.

9. A method of inhibiting factor VIIa, comprising administering to a patient an effective amount of at least one compound chosen from the compounds of the formula I as claimed in claim 1 and their physiologically tolerable salts.

10. A method of inhibiting factor VIIa, comprising contacting a sample which contains factor VIIa with at least one compound chosen from the compounds of the formula I as claimed in claim 1 and their physiologically tolerable salts.

11. A method of inhibiting or reducing blood clotting or inflammatory response, comprising administering to a patient an effective amount of at least one compound chosen from the compounds of the formula I as claimed in claim 1 and their physiologically tolerable salts.

12. A method of treating cardiovascular disorders, thromboembolic diseases or restenoses, comprising administering to a patient an effective amount of at least one compound chosen from the compounds of the formula I as claimed in claim 1 and their physiologically tolerable salts.

* * * * *

UNITED STATES PATENT AND TRADEMARK OFFICE
CERTIFICATE OF CORRECTION

PATENT NO. : 6,743,790 B2
DATED : June 1, 2004
INVENTOR(S) : Otmar Klingler et al.

It is certified that error appears in the above-identified patent and that said Letters Patent is hereby corrected as shown below:

Column 37,
Lines 62-63, "$(C_6-C_{14})$- aryl-$(C_1-C_4)$-alkoxycarbonyl-," should read
-- $(C_6-C_{14})$-aryl-$(C_1-C_4)$-alkoxycarbonyl-, --.

Column 38,
Lines 2-3, "$R^{20}$-$(C_6-C_{12})$-alkyl-," should read -- $R^{20}$-$(C_1-C_{12})$-alkyl-, --.
Line 3, "$R^{20}$-$(C_1-C_{14})$-aryl-," should read -- $R^{20}$-$(C_6-C_{14})$-aryl-, --.
Line 10, "$(C_6-C_{14})$,-aryl," should read -- $(C_6-C_{14})$-aryl, --.
Line 11, "$(C_8-C_{14}$-aryl-$(C_1-C_4)$-alkyl-," should read -- $(C_6-C_{14})$-aryl-$(C_1-C_4)$-alkyl-, --.
Line 42, "$(C^6-C_{14})$-aryl," should read -- $(C_6-C_{14})$-aryl, --; and "Het-$(C_1-C_4,$-alkyl-," should read -- Het-$(C_1-C_4)$-alkyl-, --.
Line 51, "$(C_6-C_{14}$-aryl-$(C_1-C_4)$-alkylaminocarbonyl-," should read
-- $(C_6-C_{14})$-aryl-$(C_1-C_4)$-alkylaminocarbonyl-, --.

Column 39,
Line 12, "$(C_6-C_{14}$-aryl-$(C_1-C_4)$-alkoxy-," should read
-- $(C_6-C_{14})$-aryl-$(C_1-C_4)$-alkoxy-, --.

Column 40,
Line 8, "In formula" should read -- in formula --.
Lines 33-34, "$(C_1-C_8)$-alkoxycarbonylamino," should read
-- $(C_1-C_6)$-alkoxycarbonylamino, --.
Line 42, "$R^3$;" should read -- $R^3$, --.

Signed and Sealed this

Twenty-first Day of December, 2004

JON W. DUDAS
*Director of the United States Patent and Trademark Office*